(12) United States Patent
Yoshiara et al.

(10) Patent No.: US 9,763,645 B2
(45) Date of Patent: Sep. 19, 2017

(54) ULTRASOUND APPARATUS AND ULTRASOUND APPARATUS CONTROLLING METHOD AND NON-TRANSITORY COMPUTER READABLE MEDIUM

(75) Inventors: Hiroki Yoshiara, Nasushiobara (JP); Naohisa Kamiyama, Otawara (JP); Tetsuya Yoshida, Nasushiobara (JP); Yoko Okamura, Nasushiobara (JP); Yuko Kanayama, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1054 days.

(21) Appl. No.: 13/613,001

(22) Filed: Sep. 13, 2012

(65) Prior Publication Data
US 2013/0006108 A1 Jan. 3, 2013

Related U.S. Application Data

(63) Continuation of application No. PCT/JP2011/080301, filed on Dec. 27, 2011.

(30) Foreign Application Priority Data

Dec. 27, 2010 (JP) .................................. 2010-291087

(51) Int. Cl.
*A61B 8/00* (2006.01)
*A61B 8/08* (2006.01)
(Continued)

(52) U.S. Cl.
CPC ............ *A61B 8/481* (2013.01); *G01S 7/5202* (2013.01); *G01S 7/52085* (2013.01);
(Continued)

(58) Field of Classification Search
CPC ........... A61B 8/06; A61B 8/14; A61B 8/4488; A61B 8/465; A61B 8/466; A61B 8/469;
(Continued)

(56) References Cited

U.S. PATENT DOCUMENTS 4,865,042 A 9/1989 Umemura et al.
5,301,168 A * 4/1994 Miller ........................... 367/138
(Continued)

FOREIGN PATENT DOCUMENTS

JP 59-37940 3/1984
JP 62-87151 4/1987
(Continued)

OTHER PUBLICATIONS

International Search Report and Written Opinion issued Feb. 21, 2012, in International application No. PCT/JP2011/080301.
(Continued)

*Primary Examiner* — Amanda Lauritzen Moher
(74) *Attorney, Agent, or Firm* — Oblon, McClelland, Maier & Neustadt, L.L.P.

(57) ABSTRACT

An ultrasound apparatus according to the present embodiments includes a receiving unit and a probe controlling unit. The receiving unit receives settings in relation to the aperture of the ultrasound probe and the region of interest of the subject with a contrast agent injected. The probe controlling unit controls the ultrasound probe based on the settings received by the receiving unit in such a manner as to transmit an ultrasound wave from the vibrator arranged in the aperture to the region of interest.

13 Claims, 15 Drawing Sheets

(51) Int. Cl.
*G01S 7/52* (2006.01)
*G01S 15/89* (2006.01)
*A61B 8/06* (2006.01)
*A61B 8/14* (2006.01)

(52) U.S. Cl.
CPC ...... *G01S 15/8927* (2013.01); *G01S 15/8952* (2013.01); *A61B 8/06* (2013.01); *A61B 8/14* (2013.01); *A61B 8/4488* (2013.01); *A61B 8/465* (2013.01); *A61B 8/466* (2013.01); *A61B 8/469* (2013.01); *A61B 8/483* (2013.01); *A61B 8/5246* (2013.01); *A61B 8/54* (2013.01); *G01S 7/52074* (2013.01); *G01S 15/8993* (2013.01)

(58) Field of Classification Search
CPC ....... A61B 8/481; A61B 8/483; A61B 8/5246; A61B 8/54; G01S 15/8927; G01S 15/8952; G01S 15/8993; G01S 7/5202; G01S 7/52074
See application file for complete search history.

(56) References Cited

U.S. PATENT DOCUMENTS

| | | | | |
|---|---|---|---|---|
| 5,844,140 | A * | 12/1998 | Seale | A61B 8/08 310/90.5 |
| 5,971,927 | A * | 10/1999 | Mine | A61B 8/06 600/455 |
| 6,186,951 | B1 * | 2/2001 | Lizzi | A61B 8/06 600/458 |
| 6,245,017 | B1 | 6/2001 | Hashimoto et al. | |
| 6,475,148 | B1 * | 11/2002 | Jackson | A61B 8/481 600/439 |
| RE38,971 | E * | 2/2006 | Kamiyama | A61B 8/00 600/443 |
| 8,641,626 | B2 * | 2/2014 | Yoshida | A61B 8/06 600/407 |
| 8,740,797 | B2 * | 6/2014 | Ogihara et al. | 600/439 |
| 2002/0022780 | A1 | 2/2002 | Kawagishi et al. | |
| 2002/0165455 | A1 | 11/2002 | Lysyansky | |
| 2003/0023166 | A1 | 1/2003 | Frisa et al. | |
| 2004/0215076 | A1 * | 10/2004 | Kamiyama | A61B 8/06 600/443 |
| 2004/0267128 | A1 | 12/2004 | Matsumura | |
| 2005/0245828 | A1 * | 11/2005 | Tsujino | G01S 7/52071 600/453 |
| 2006/0116582 | A1 * | 6/2006 | Yoshida | A61B 8/06 600/458 |
| 2007/0265530 | A1 | 11/2007 | Hashimoto et al. | |
| 2008/0095415 | A1 * | 4/2008 | Hall | A61B 8/0883 382/128 |
| 2008/0262354 | A1 * | 10/2008 | Yoshida | A61B 8/469 600/443 |
| 2010/0222676 | A1 | 9/2010 | Ogihara et al. | |

FOREIGN PATENT DOCUMENTS

| | | |
|---|---|---|
| JP | 2000-135217 | 5/2000 |
| JP | 2001-327505 | 11/2001 |
| JP | 2002-165795 | 6/2002 |
| JP | 2002-253548 | 9/2002 |
| JP | 2002-360576 | 12/2002 |
| JP | 2003-93389 | 4/2003 |
| JP | 2003-230560 | 8/2003 |
| JP | 2005-537078 | 12/2005 |
| JP | 2007-313294 | 12/2007 |
| JP | 2008-178590 | 8/2008 |
| JP | 2009-100927 A | 5/2009 |
| WO | WO 2006/137484 A1 | 12/2006 |

OTHER PUBLICATIONS

Katsuro Tachibana, "Application of Microbubbles for Therapy", Medical and Biological Engineering, 43 (2), 2005, pp. 211-215 (with partial English translation).

Nobuki Kudo, et al., "Sonoporation with Microbubbles Exposed to Pulsed Ultrasound", Medical and Biological Engineering, 43 (2), 2005, pp. 231-237 (with partial English translation).

E. Unger, et al., "Microbubbles in molecular imaging and therapy" MEDICAMUNDI 47/1, Apr. 2003, pp. 58-65.

Mark A. Borden, et al., "Influence of Lipid Shell Physicochemical Properties on Ultrasound-Induced Microbubble Destruction", IEEE Trans UFFC, Nov. 2005, 52(11) : 1992-2002, pp. 1-28.

Office Action issued on Oct. 7, 2014 in Japanese Patent Application No. 2010-291087 with English translation.

* cited by examiner

FIG.11
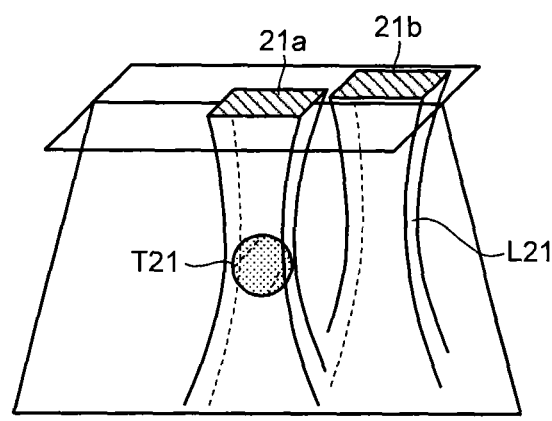
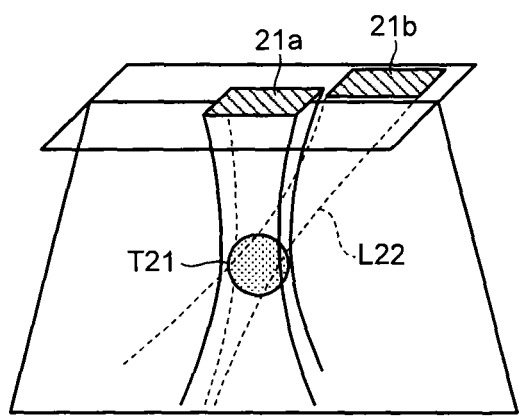

| PATTERN | SCANNING LINE | TRANSMISSION CONDITION | | | |
|---|---|---|---|---|---|
| | | SOUND PRESSURE | FREQUENCY | PRF | ... |
| PT11 | L11 | P10 | F5 | RF10 | ... |
| | L12 | P10 | F5 | RF10 | ... |
| | L13 | P10 | F5 | RF10 | ... |
| | L14 | P10 | F5 | RF10 | ... |
| | L15 | P10 | F5 | RF10 | ... |
| | ... | ... | ... | ... | ... |
| PT12 | L11 | P10 | F5 | RF5 | ... |
| | L12 | P5 | F6 | RF5 | ... |
| | L13 | P5 | F7 | RF5 | ... |
| | L14 | P5 | F8 | RF5 | ... |
| | L15 | P5 | F9 | RF5 | ... |
| | ... | ... | ... | ... | ... |
| PT13 | L11 | P10 | F5 | RF10 | ... |
| | L12 | P5 | F6 | RF10 | ... |
| | L13 | P5 | F7 | RF10 | ... |
| | L14 | P5 | F8 | RF10 | ... |
| | L15 | P5 | F9 | RF10 | ... |
| | ... | ... | ... | ... | ... |
| | ... | ... | ... | ... | ... |

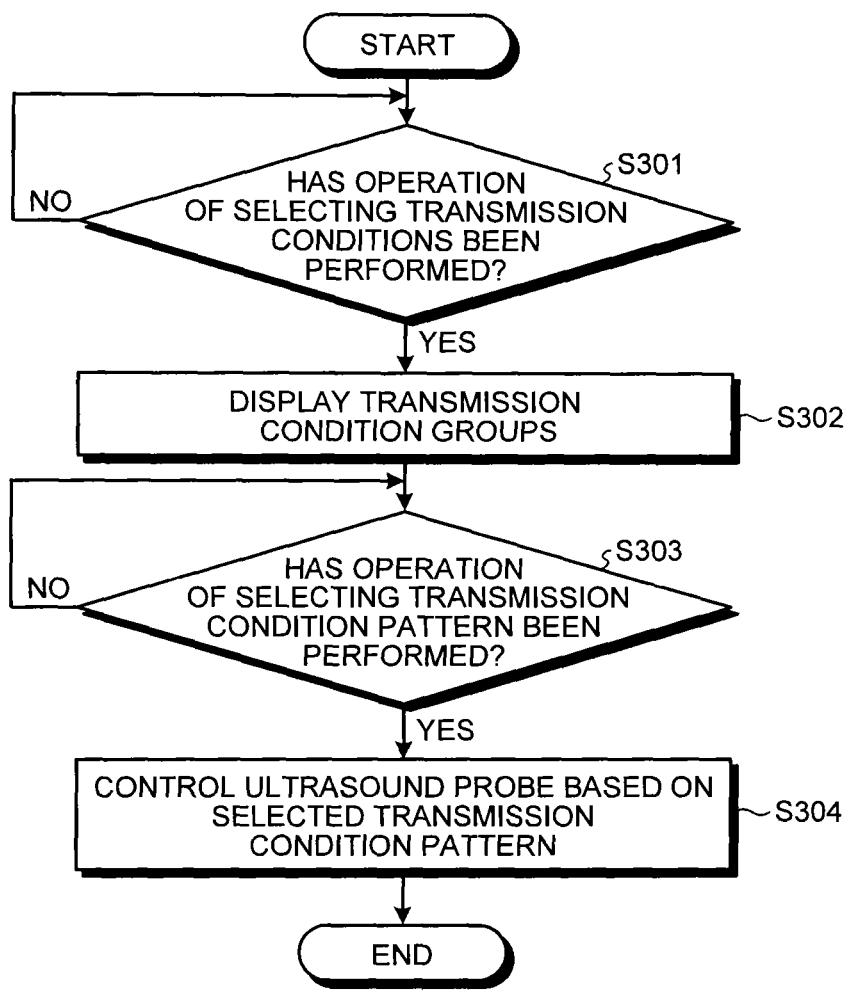

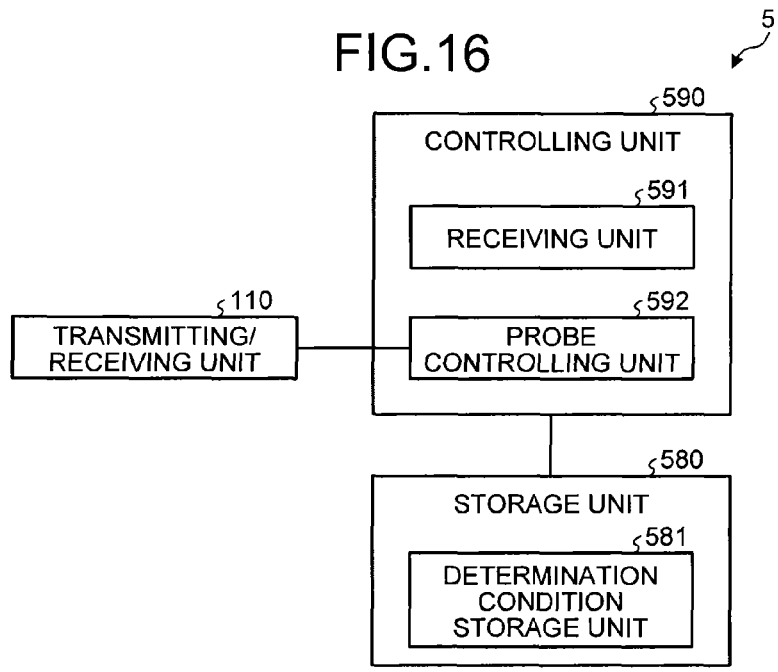

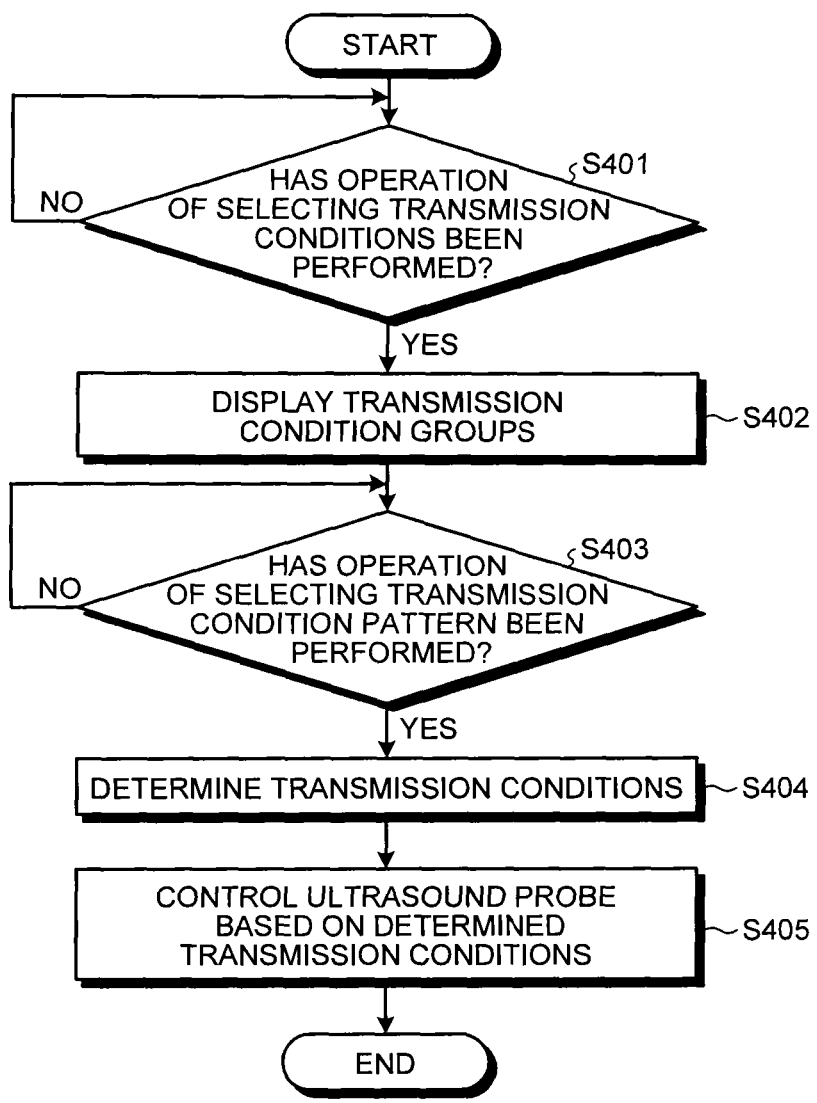

ULTRASOUND APPARATUS AND ULTRASOUND APPARATUS CONTROLLING METHOD AND NON-TRANSITORY COMPUTER READABLE MEDIUM

CROSS-REFERENCE TO RELATED APPLICATIONS

This application is a continuation of PCT international application Ser. No. PCT/JP2011/080301 filed on Dec. 27, 2011 which designates the United States, and which claims the benefit of priority from Japanese Patent Application No. 2010-291087, filed on Dec. 27, 2010; the entire contents of which are incorporated herein by reference.

FIELD

Embodiments described herein relate generally to an ultrasound apparatus and an ultrasound apparatus controlling method and a non-transitory computer readable medium.

BACKGROUND

An ultrasound diagnosis apparatus has been used for tests and diagnosis for various body tissues such as the heart, liver, kidney, and mammary gland. Recently, an ultrasonic contrast agent (hereinafter, "contrast agent") of an intravenous administration type has been commercially introduced, and the contrast echo method has been used. With the contrast echo method, minute bubbles (hereinafter, "microbubbles") or the like are intravenously administered as a contrast agent to enhance the blood-flow signals, realizing clear observation of the blood flowing state.

Furthermore, research has been conducted on application of ultrasound to medical treatment. Through such research, it has been confirmed that, when emitting ultrasound waves onto the subject, pores are temporarily formed in cells by mechanical action of cavitation, and that they make genes and medicinal substances easy to permeate into the cells. It has also been confirmed that, when microbubbles are injected, pores are temporarily formed in cells by mechanical action of cavitation of the microbubbles even if the ultrasonic sound pressure is low, and that they enhance the permeation of genes and medicinal substances into the cells. The phenomenon that ultrasonic irradiation improves the permeation of genes or medical substances into the cells is sometimes called as "sonopolation".

The problem to be solved by the present invention is to present an ultrasound apparatus that can enhance the penetration of genes and medicinal substances into a specific site by use of microbubbles, and a controlling method and a non-transitory computer readable medium for such an ultrasound apparatus.

BRIEF DESCRIPTION OF THE DRAWINGS

FIG. 11 is a diagram for explaining an example of the process performed by the controlling unit according to the second embodiment;

FIG. 14 is a diagram for showing an example of a transmission condition storage unit;

FIG. 15 is a flowchart of an example procedure of the process performed by the controlling unit according to the fourth embodiment;

FIG. 16 is a block diagram for showing an example structure of the storage unit and the controlling unit according to the fifth embodiment;

FIG. 17 is a diagram for showing an example of a decision condition storage unit; and FIG. 18 is a flowchart of an example procedure of a process performed by the controlling unit according to the fifth embodiment.

DETAILED DESCRIPTION

The ultrasound apparatus according to the present embodiments includes a receiving unit and a probe controlling unit. The receiving unit receives the settings in relation to the transmission condition of an ultrasound wave for each scanning line of the ultrasound wave transmitted by an ultrasound probe. The probe controlling unit controls the ultrasound probe in accordance with the transmission condition that is received by the receiving unit for each scanning line so that the ultrasound wave is emitted to the subject with a contrast agent injected.

First Embodiment

Figure 1:
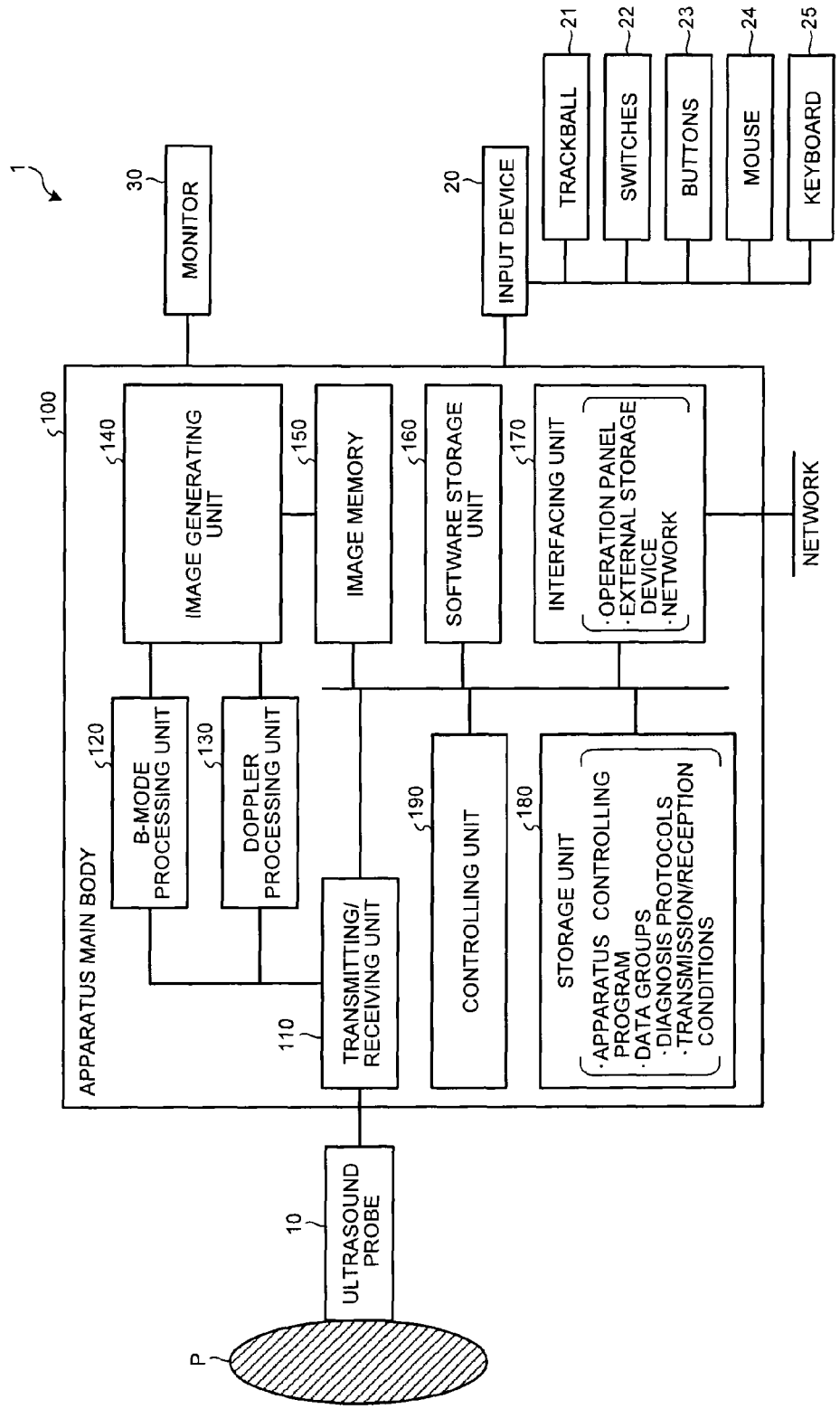
FIG. 1 is a block diagram for showing an example structure of an ultrasound apparatus according to the first embodiment.

First, the structure of the ultrasound apparatus according to the first embodiment is explained with reference to FIG. 1. FIG. 1 is a block diagram for showing an example structure of the ultrasound apparatus according to the first embodiment. An ultrasound apparatus 1 illustrated in FIG. 1 can be used as an ultrasound diagnosis apparatus for conducting a diagnosis of a subject, or as an ultrasound treatment apparatus for providing a subject with treatment. Such an ultrasound apparatus 1 includes an ultrasound probe 10, an input device 20, a monitor 30, and an apparatus main body 100, as illustrated in FIG. 1.

The ultrasound probe 10 includes multiple piezoelectric vibrators, and these piezoelectric vibrators generate ultrasound waves in accordance with a drive signal supplied from a later-described transmitting/receiving unit 110 of the apparatus main body 100. Furthermore, the ultrasound probe 10 receives reflection signals from the subject P and converts them to electric signals. The ultrasound probe 10 also includes a matching layer arranged on the piezoelectric vibrators, a backing material that prevents the ultrasound waves from propagating backward from the piezoelectric vibrators, and the like. The ultrasound probe 10 is detachably connected to the apparatus main body 100.

When an ultrasound wave is transmitted from the ultrasound probe 10 to the subject P, the transmitted ultrasound wave is reflected sequentially from the surface of the body tissue of the subject P where the acoustic impedance is discontinuous, and received as a reflection wave signal by multiple piezoelectric vibrators included in the ultrasound probe 10. The amplitude of the received reflection wave signal depends on the difference in the acoustic impedances that appear on the discontinuous surface where the ultrasound wave is reflected. The reflection wave signal obtained when a transmitted ultrasonic pulse is reflected from the flowing bloodstream or a surface such as the cardiac wall depends on the velocity component of the moving target with respect to the transmission direction of the ultrasound wave because of the Doppler effect, and its frequency is thereby shifted.

The input device 20 is connected to the apparatus main body 100, and includes a trackball 21, various switches 22, various buttons 23, a mouse 24, a keyboard 25, and the like. Such an input device 20 captures various instructions from the operator, an instruction on the setting of the region of interest (ROI), an instruction on the setting of image quality conditions of an ultrasonic image, and the like into the apparatus main body 100.

The monitor 30 displays a graphical user interface (GUI) for the operator of the ultrasound apparatus 1 to perform various settings by use of the input device 20, and also displays ultrasonic images generated by the apparatus main body 100. More specifically, the monitor 30 displays morphological information or bloodstream information of the living body as an image, in accordance with video signals input from a later-described image generating unit 140.

The apparatus main body 100 generates an ultrasonic image in accordance with the reflection wave signals received by the ultrasound probe 10. As illustrated in FIG. 1, the apparatus main body 100 includes a transmitting/receiving unit 110, a B-mode processing unit 120, a Doppler processing unit 130, an image generating unit 140, an image memory 150, a software storage unit 160, an interfacing unit 170, a storage unit 180, and a controlling unit 190. The transmitting/receiving unit 110, the B-mode processing unit 120, the Doppler processing unit 130, the image generating unit 140, and the like that are arranged inside the apparatus main body 100 may be realized by hardware such as an integrated circuit or by a software program that is modularized in the form of software.

The transmitting/receiving unit 110 includes a delay circuit, a pulsar circuit, a trigger generating circuit and the like that are not shown, and supplies a drive signal to the ultrasound probe 10. The pulse generating circuit repeatedly generates rate pulses at a certain pulse repetition frequency (PRF) for forming a transmission ultrasound wave. The pulse repetition frequency is also referred to as a rate frequency, or the like. In addition, the delay circuit gathers the ultrasound wave emitted from the ultrasound probe 10 into a beam, and also gives each rate pulse a delay time for each piezoelectric vibrator that is necessary to determine the transmission directionality. Moreover, the trigger generating circuit applies a drive signal (drive pulse) to the ultrasound probe 10 at a timing based on each rate pulse to which a delay time is given by the delay circuit. The transmission direction or the delay time that determines the transmission direction is stored in the storage unit 180, and the delay circuit gives the delay time by referring to the storage unit 180.

In addition, the transmitting/receiving unit 110 has an amplifying circuit, an analog/digital (A/D) converter, an adder, and the like that are not shown, and it performs various kinds of processing onto the reflection wave signals received by the ultrasound probe 10 to generate reflection wave data. The amplifying circuit amplifies the reflection wave signals for different channels. The A/D converter performs A/D conversion onto the amplified reflection wave signals, and gives them a delay time that is necessary to determine the reception directionality. The adder performs an adding process onto the reflection wave signals to which the delay time is given and generates reflection wave data. Through the adding process performed by the adder, the reflection component of the reflection wave signal from a direction corresponding to the reception directionality is enhanced, and thereby an ultrasonic transmission/reception total beam is formed in accordance with the reception directionality and the transmission directionality. In a similar manner as the transmission, the reception direction or the delay time for determining the reception direction is stored in the storage unit 180.

The transmitting/receiving unit 110 has a function of instantly changing the delay information, the transmission frequency, the transmission driving voltage, the number of aperture elements, and the like according to an instruction from the controlling unit 190. Especially when the transmission driving voltage is to be changed, it is realized by a linear-amplifier transmitting circuit that can instantly switch its value, or a mechanism that can electrically switch multiple power supply units. In this manner, the transmitting/receiving unit 110 controls the transmission directionality and the reception directionality in the ultrasonic transmission and reception.

The B-mode processing unit 120 receives the reflection wave data from the transmitting/receiving unit 110, performs logarithmic amplification and envelope detection processing and the like thereon, and thereby generates data that expresses the signal intensity in brightness level (B-mode data).

Here, the B-mode processing unit 120 can change the frequency band for imaging by changing the detection frequency. Moreover, the B-mode processing unit 120 can perform detection processing onto one piece of reflection wave data by use of two detection frequencies in parallel. By using the function of the B-mode processing unit 120, the reflection wave data of the subject P with microbubbles injected can be separated into the reflection wave data that is reflected from the microbubbles and generated from a band signal of a sub-harmonic or a higher harmonic wave of the transmission frequency, and the reflection wave data that is reflected from the tissue of the subject P and generated from a band signal of a fundamental wave corresponding to the transmission frequency. In other words, the B-mode processing unit 120 can generate B-mode data for generating a contrast enhanced image, as well as B-mode data for generating a tissue image. As a result, the later-described image generating unit 140 can generate a contrast enhanced image that visualizes the contrast agent flowing inside the subject P with a high sensitivity and a tissue image that visualizes the tissue.

The above transmitting/receiving unit 110 can also transmit different waveforms for different ultrasonic scanning lines. For example, if pulse inversion, which is an imaging method of generating a contrast enhanced image with the second-order harmonic component enhanced, is to be implemented, the transmitting/receiving unit 110 transmits a waveform that is 180 degrees out of phase with the waveform of the first transmission (i.e., a waveform the amplification of which is inverted) for the second time, and thereby generates reflection wave data for each. Then, the B-mode processing unit 120 adds up the two pieces of reflection wave data received from the transmitting/receiving unit 110 so that a signal in which the fundamental component is suppressed while the second harmonic component is doubled can be acquired.

The Doppler processing unit 130 performs a frequency analysis onto the velocity information from the reflection wave data received from the transmitting/receiving unit 110, extracts echo components of the bloodstream, the tissue, and the contrast agent by using the Doppler effect, and calculates the bloodstream information such as average velocity, distribution, and power at multiple points.

The image generating unit 140 generates a B-mode image in which the signal intensity is expressed in brightness level, from the B-mode data generated by the B-mode processing unit 120, and generates a color Doppler image that displays power components and the like indicating the blood flow rate, distribution, and blood flow volume in colors in a distinguishable manner, from the bloodstream information generated by the Doppler processing unit 130. The data before being input to the image generating unit 140 may be referred to as "raw data".

More specifically, the image generating unit 140 includes a signal processing unit, a scan converter, and an image processing unit that are not shown. The signal processing unit executes a filtering process onto the B-mode data and the Doppler data to remove noise components from an ultrasonic scanning line signal string, and stores the data that is subjected to the filtering process into the image memory 150. The scan converter converts the ultrasonic scanning line signal string of the data subjected to the filtering process by the signal processing unit to a scanning line signal string in common video format such as for TV. The image processing unit executes, onto the scanning line signal string that is output from the scan converter, the brightness and contrast adjusting process, the imaging process such as space filtering, or the process of combining character information of various setting parameters and memories, and outputs it as a video signal onto the monitor 30. In this manner, an ultrasonic image such as a tomographic image that is generated by the image generating unit 140 to show the shape of the tissue of the subject is displayed onto the monitor 30.

The image memory 150 is a memory that stores therein ultrasonic images generated by the image generating unit 140 and images generated by performing image processing onto an ultrasonic image. For example, after a diagnosis, the operator is allowed to retrieve an image stored during a test from the image memory 150 and to reproduce it as a still image or reproduce multiple images as a moving video. Furthermore, the image memory 150 stores image brightness signals that have passed through the transmitting/receiving unit 110, other raw data, images acquired through the network, and the like, as need arises.

The software storage unit 160 is a storage area in which various apparatus controlling programs are expanded by the later-described controlling unit 190.

The interfacing unit 170 is an interface for the input device 20, a new external storage device (not shown in the drawings), and the network. The data obtained by the ultrasound apparatus 1 such as an ultrasonic image can be transferred to another apparatus by the interfacing unit 170 by way of a network.

The storage unit 180 stores therein various apparatus controlling programs for executing scan sequences, image processing, display processing and the like, and various data groups such as diagnosis information (e.g., subject IDs and doctor's remarks), diagnosis protocols and various setting information. The apparatus controlling programs may include a program that describes the procedure of a process similar to the one performed by the controlling unit 190. Moreover, the storage unit 180 is also used to maintain ultrasonic images stored in the image memory 150 if necessary. The data stored in the storage unit 180 may be transmitted to an external peripheral device by way of the interfacing unit 170.

The controlling unit 190 is a controlling processor (central processing unit or CPU) that realizes a function of an information processing apparatus (computer), and it controls the entire processing of the ultrasound apparatus 1. More specifically, the controlling unit 190 expands various instructions input by the operator through the input device 20 and setting instructions and various apparatus controlling programs read from the storage unit 180 onto the software storage unit 160, controls the processing of the transmitting/receiving unit 110, the B-mode processing unit 120, the Doppler processing unit 130, and the image generating unit 140 in accordance with various kinds of setting information, and also performs control in such a manner that an ultrasonic image stored in the image memory 150 or the like can be displayed on the monitor 30.

The overall structure of the ultrasound apparatus 1 according to the first embodiment has been explained above. With such a structure, the ultrasound apparatus 1 according to the first embodiment makes the operator set ultrasonic transmission conditions for each scanning line of the ultrasound wave emitted by the ultrasound probe 10. Then, when ultrasonic transmission conditions are set for each scanning line, the ultrasound apparatus 1 controls the ultrasound probe 10 in such a manner as to emit an ultrasound wave in accordance with the transmission conditions of the scanning line. In other words, the ultrasound apparatus 1 can apply ultrasound waves to the subject P in accordance with transmission conditions that differ depending on a spatial position.

The "ultrasonic transmission conditions" here mean various conditions of ultrasound waves transmitted by the ultrasound probe 10. For example, they indicate the sound pressure, the frequency, the pulse repetition frequency, the transmission rate that is the number of signals used for generating one ultrasonic beam, the waveform, and the like regarding each ultrasound wave.

The ultrasound apparatus 1 can change the ultrasonic transmission conditions for individual scanning lines, for example, when an ultrasound wave is applied to the subject P to whom microbubbles are injected, and thus it can break or fractionate microbubbles at a specific site that the operator desires or can create cavitation by resonating the microbubbles with the ultrasound wave. In this manner, the ultrasound apparatus 1 can inject microbubbles into even a small blood vessel such as a capillary at a specific site. Furthermore, if microbubbles that contain medicinal substances are injected to the subject P, the ultrasound apparatus 1 can accelerate the permeation of the medicine through a specific treatment site such as a blood vessel or a tumor. The ultrasound apparatus 1 according to the first embodiment is explained in detail below with reference to FIGS. 2 to 7. In the explanation below, it is assumed that the microbubbles contain a medicinal substance.

Figure 2:
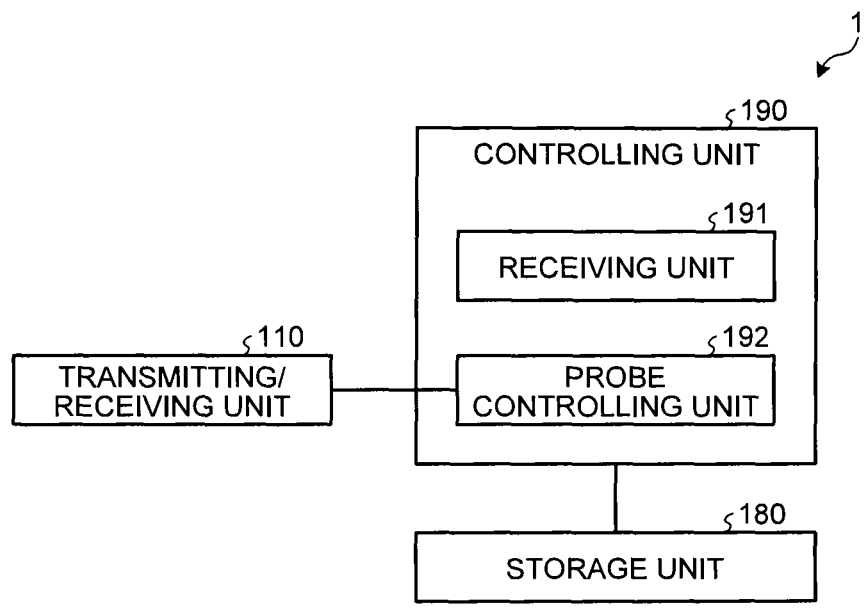
FIG. 2 is a block diagram for showing an example structure of a controlling unit according to the first embodiment.

FIG. 2 is a block diagram for showing an example structure of the controlling unit 190 according to the first embodiment. As illustrated in FIG. 2, the controlling unit 190 includes a receiving unit 191 and a probe controlling unit 192.

The receiving unit 191 receives the settings for the ultrasonic transmission conditions for each scanning line of the ultrasound wave emitted by the ultrasound probe 10. For example, when the operator performs an operation of setting the ultrasonic transmission condition by use of the input device 20, the receiving unit 191 receives the settings of the ultrasonic transmission conditions for each scanning line from the input device 20. Then, when receiving the ultrasonic transmission conditions, the receiving unit 191 stores the received transmission conditions into the storage unit 180, a not-shown internal memory, or the like.

The operator may input the ultrasonic transmission conditions for each scanning line, for example, by use of the keyboard 25. Furthermore, if the ultrasound apparatus 1 displays transmission condition options onto the monitor 30, the operator may select an ultrasonic transmission condition, for example, from among the transmission condition options displayed on the monitor 30, by use of the trackball 21, the mouse 24, or the like.

The probe controlling unit 192 controls the ultrasound probe 10 in such a manner as to transmit an ultrasound wave in accordance with the transmission conditions received for individual scanning lines by the receiving unit 191. For example, when the receiving unit 191 stores the transmission conditions for the individual scanning lines in the storage unit 180, the probe controlling unit 192 controls the ultrasonic transmission process performed by the ultrasound probe 10 for the individual scanning lines by use of the transmission conditions stored for the individual scanning lines in the storage unit 180.

Figure 3:
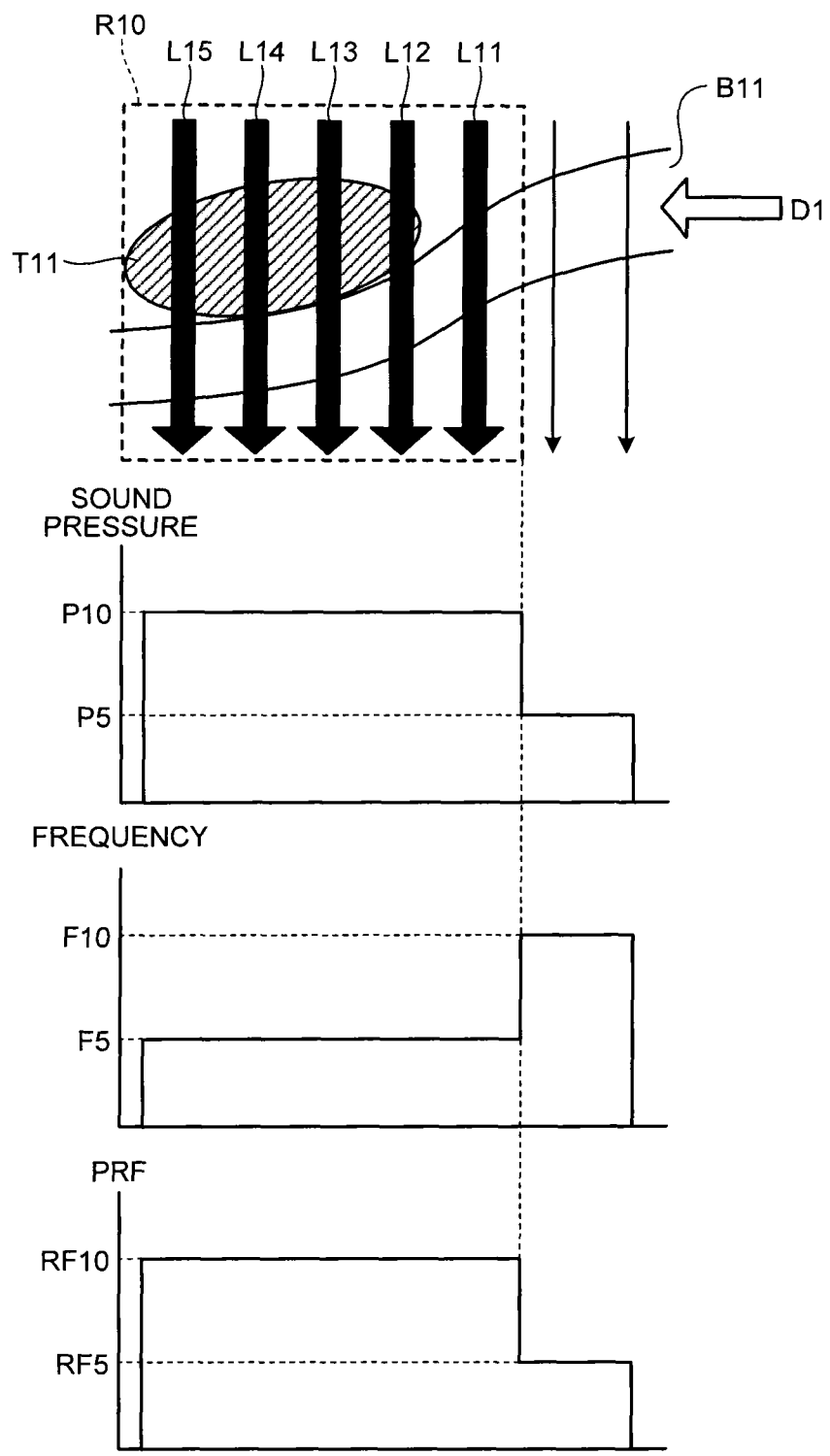
FIG. 3 is a diagram for showing an example of an ultrasound transmitting process performed by the ultrasound apparatus according to the first embodiment.
Figure 4:
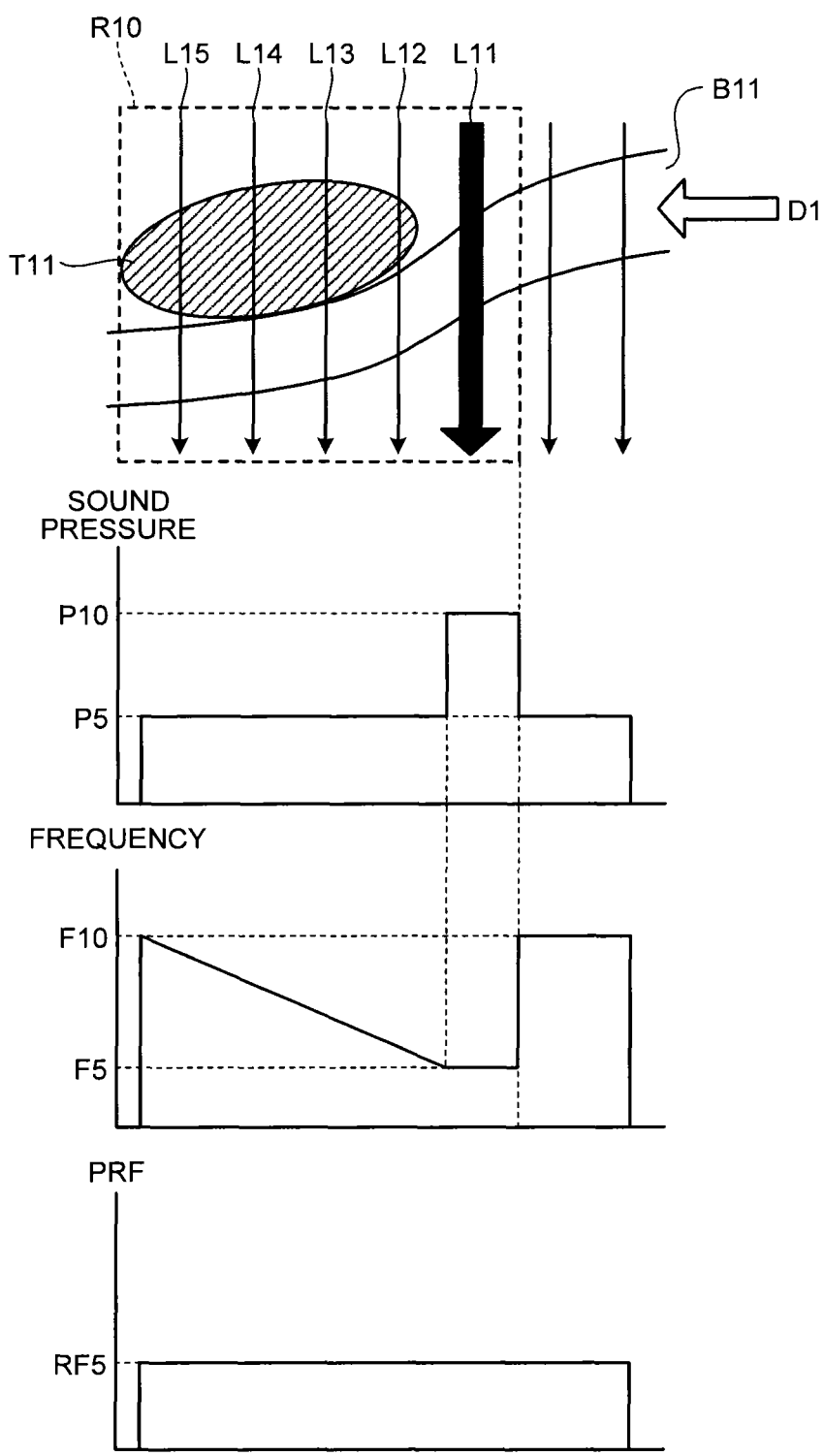
FIG. 4 is a diagram for showing an example of the ultrasound transmitting process performed by the ultrasound apparatus according to the first embodiment.
Figure 5:
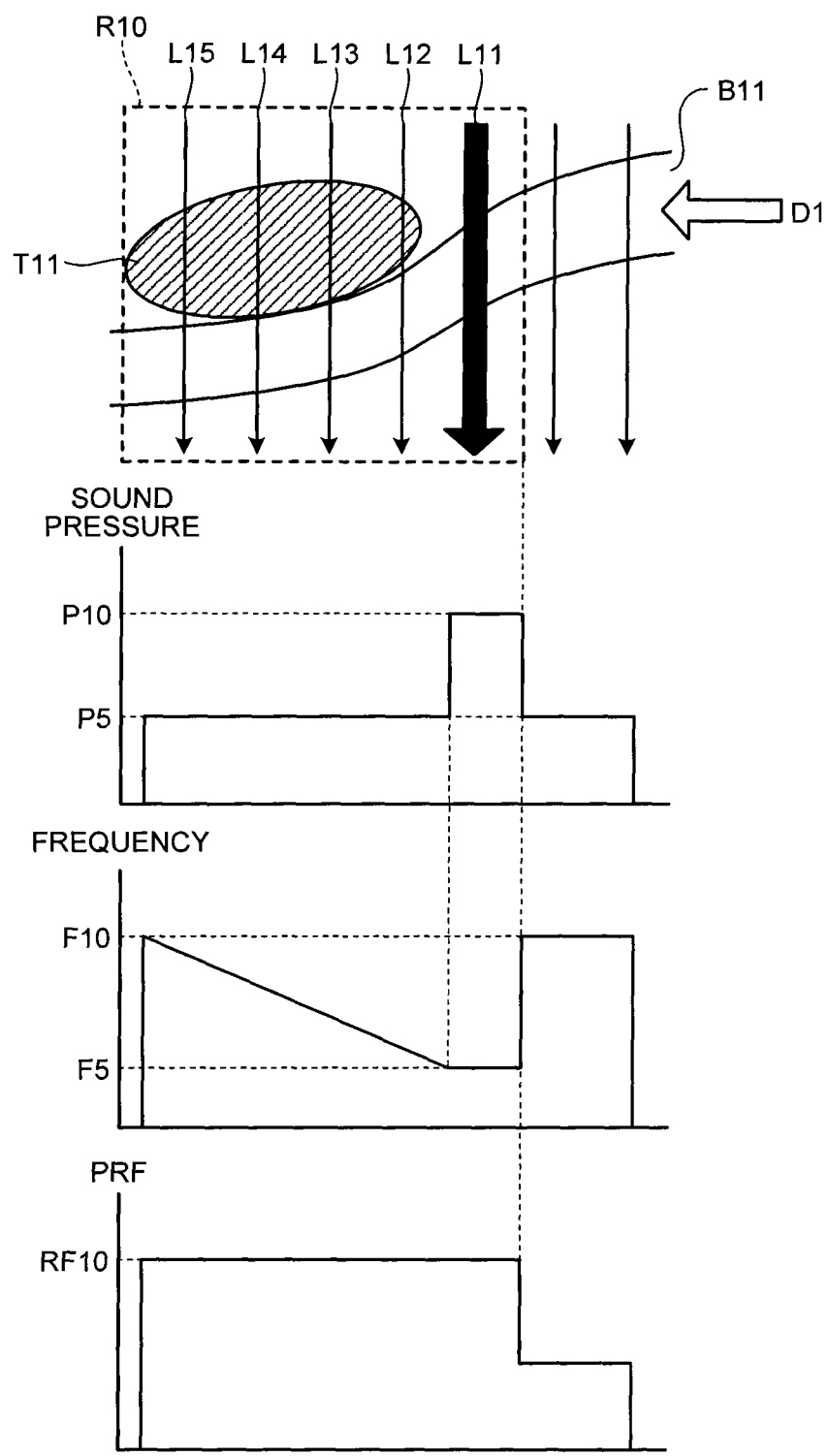
FIG. 5 is a diagram for showing an example of the ultrasound transmitting process performed by the ultrasound apparatus according to the first embodiment.

Next, an example of the ultrasound transmitting process performed by the ultrasound apparatus 1 according to the first embodiment is explained with reference to FIGS. 3 to 5. FIGS. 3 to 5 are diagrams for showing examples of the ultrasound transmitting process performed by the ultrasound apparatus 1 according to the first embodiment. In FIGS. 3 to 5, examples in which an ultrasound wave is transmitted to a region of interest R10 are illustrated.

In the examples of FIGS. 3 to 5, a treatment site T11 is located in the vicinity of a blood vessel B11 having a blood flow direction D1, and microbubbles containing a medicinal substance is injected to the blood vessel B11. Furthermore, for the ultrasound apparatus 1 according to the first embodiment, it is preferable that the sound pressure of the ultrasound wave is "P5", the frequency of the ultrasound wave is "F10", and the pulse repetition frequency of the ultrasound wave is "RF5".

First, an example of FIG. 3 is explained. In the example of FIG. 3, the purpose is to permeate the medicinal substance throughout the treatment site T11. More specifically, in the example of FIG. 3, a sound pressure "P10", which is higher than the sound pressure "P5" for generating an ultrasonic image, is set for the ultrasound wave in the scanning lines L11 to L15. In this manner, an ultrasound wave having the high sound pressure "P10" is emitted to the entire region of interest R10, which makes the microbubbles in the blood vessel B11 easy to break. In other words, in the example of FIG. 3, the ultrasound apparatus 1 can break microbubbles in the vicinity of the treatment site T11, and as a result, the permeation of the medicinal substance into the treatment site T11 can be accelerated.

In addition, as illustrated in FIG. 3, a frequency "F5", which is lower than the frequency "F10" adopted for generating an ultrasonic image, is set for the ultrasound wave in the scanning lines L11 to L15. To explain this point, microbubbles are easier to break with an ultrasound wave of a lower frequency, as can be seen from the fact that a mechanical index (MI) that is an index of ultrasonic action to the living body with cavitation is represented by a value obtained by dividing the negative sound pressure by the square root of the frequency. In the example of FIG. 3, the purpose is to permeate the medicinal substance throughout the treatment site T11. Thus, if the frequency of the ultrasound wave is set low, the microbubbles become easy to break. As a result, the ultrasound apparatus 1 can accelerate the permeation of the medicinal substance into the treatment site T11.

Furthermore, as illustrated in FIG. 3, a "RF10", which is higher than the pulse repetition frequency "RF5" adopted for generating an ultrasonic image, is set for the pulse repetition frequency of the ultrasound wave in the scanning lines L11 to L15. By setting the pulse repetition frequency high, the number of ultrasonic pulses emitted from the ultrasound probe 10 per unit time increases. This breaks or fractionates the microbubbles inside the blood vessel B11 more effectively, and as a result, the permeation of the medicinal substance into the treatment site T11 can be accelerated. A value that is set high for the pulse repetition frequency reduces a period of time for receiving reflection wave signals from the subject P. However, in the example of FIG. 3, the purpose is to permeate the medicinal substance into the treatment site T11, and not in generation of ultrasonic images, and therefore this should not raise any problem. Thus, in the example of FIG. 3, the pulse repetition frequency "RF10" may be 30 [kHz] or greater.

As described above, in the example of FIG. 3, the sound pressure is set high, the frequency is set low, and the pulse repetition frequency is set high for the ultrasound wave that is to be applied in the vicinity of the treatment site T11. Hence, the ultrasound apparatus 1 can break or fragment the microbubbles in the vicinity of the treatment site T11, and can accelerate the permeation of the medicinal substance into the treatment site T11.

An example of FIG. 4 is now explained. In the example of FIG. 4, the purpose is to accelerate the injection of microbubbles into the treatment site T11 and generate an ultrasonic image in which the blood flowing state of small blood vessels such as capillaries is clearly shown. More specifically, in the example of FIG. 4, a sound pressure "P10", which is higher than the sound pressure "P5" adopted for generating an ultrasonic image, is set for the ultrasound wave of the scanning line L11, while the sound pressure "P5" is set for the ultrasound wave of the scanning lines L12 to L15. As shown above, by setting the sound pressure of the scanning line L11 that is applied to the site immediately before the blood reaches the treatment site T11 to "P10", microbubbles can be fragmented immediately before the treatment site T11. In this manner, the diameters of microbubbles can be reduced, and thereby the microbubbles can be injected to the capillaries and the like inside the treatment site T11.

Moreover, as shown in FIG. 4, the frequencies of the ultrasound waves in the scanning lines L11 to L15 increase from the scanning lines L11 to L12, L13, L14, and L15. In other words, the frequency gradually becomes higher as the bloodstream flows down. To explain this point, in the example of FIG. 4, because the sound pressure of the ultrasound wave in the scanning line L11 is set to "P10", microbubbles are fragmented at the position of the scanning line L11, reducing the diameters of the microbubbles. Then, because the ultrasound waves are also applied in the downstream of the blood flow, it is assumed that the diameters of the microbubbles become smaller as the bloodstream flows down. With the smaller diameter, the resonant frequency of the microbubbles resonating with the ultrasound wave increases. Thus, as shown in the example of FIG. 4, the frequency is set in such a manner as to increase gradually from the scanning line L11 to the scanning line L15 so that the microbubbles can resonate with the ultrasound waves.

In addition, as illustrated in FIG. 4, the pulse repetition frequency of the ultrasound wave in the scanning lines L11 to L15 is set to the pulse repetition frequency "RF5" that is adopted for generating an ultrasonic image. This is because the purpose is to generate an ultrasonic image in the example of FIG. 4.

As described above, in the example of FIG. 4, the sound pressure of the scanning line L11 is set high, the frequency of the ultrasound wave gradually increases in the bloodstream direction, and the pulse repetition frequency is set low. In this manner, the ultrasound apparatus 1 can fragment the microbubbles immediately before the treatment site T11. Thus, it can inject microbubbles into the capillaries or the like in the treatment site T11 and can generate an ultrasonic image that clearly shows the blood flowing state of small blood vessels.

Next, an example illustrated in FIG. 5 is explained. In the example of FIG. 5, the purpose is to inject genes or medical substances into the treatment site T11 by using cavitation of the microbubbles. More specifically, in the example of FIG. 5, the sound pressure and frequency of the ultrasound wave is set in a similar manner to the example of FIG. 4. Furthermore, as shown in FIG. 5, the pulse repetition frequency of the ultrasound wave in the scanning lines L11 to L15 is set to "RF10", which is higher than the pulse repetition frequency "RF5" that is adopted for generating an ultrasonic image.

As described above, in the example of FIG. 5, the sound pressure of the scanning line L11 that is applied to the blood vessel before the blood reaches the treatment site T11 is set high, the frequency of the ultrasound wave is set to gradually increase in the direction of the bloodstream, and the pulse repetition frequency is set high. In this manner, the ultrasound apparatus 1 can fragment microbubbles immediately before the treatment site T11 and maintain the formation of cavitation, which can accelerate the permeation of genes and medical substances into the treatment site T11. Moreover, because the pulse repetition frequency is set high, the microbubbles can be effectively fragmented and the cavitation can be maintained in the scanning line L11. For example, the ultrasound apparatus 1 can conduct treatment on the treatment site T11, by visualizing the blood flowing state in the treatment site T11 in accordance with the transmission conditions illustrated in FIG. 4, and then applying ultrasound waves in accordance with the transmission conditions illustrated in FIGS. 3 and 5.

Figure 6:
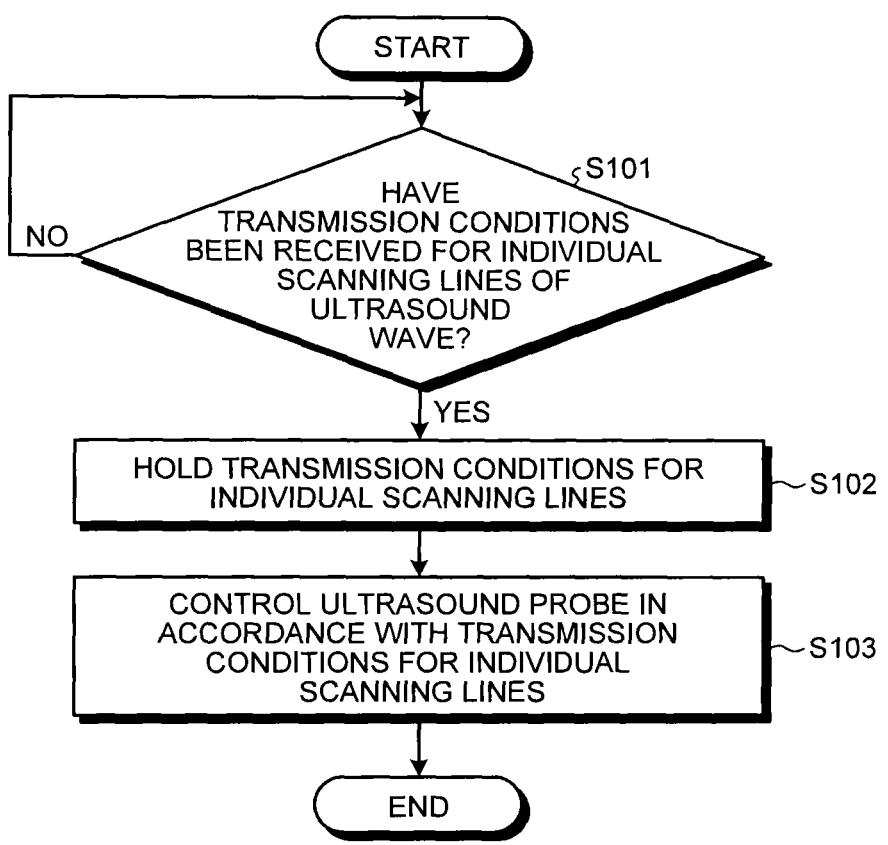
FIG. 6 is a flowchart of an example procedure of a process performed by the controlling unit according to the first embodiment.

Next, the procedure of the process performed by the controlling unit 190 according to the first embodiment is explained, with reference to FIG. 6. FIG. 6 is a flowchart of an example of the procedure of the process performed by the controlling unit 190 according to the first embodiment.

As indicated in FIG. 6, the receiving unit 191 of the ultrasound apparatus 1 determines whether the result of the operation of setting a transmission condition of the ultrasound wave for each scanning line is received (step S101). Here, if no transmission condition for a scanning line is received (no at step S101), the receiving unit 191 goes into standby mode.

On the other hand, when a transmission condition for a scanning line is received (yes at step S101), the receiving unit 191 holds the received transmission condition for each scanning line (step S102). Thereafter, the probe controlling unit 192 controls the ultrasound probe 10 in such a manner as to emit an ultrasound wave in accordance with the transmission condition received by the receiving unit 191 for each scanning line (step S103).

Figure 7:
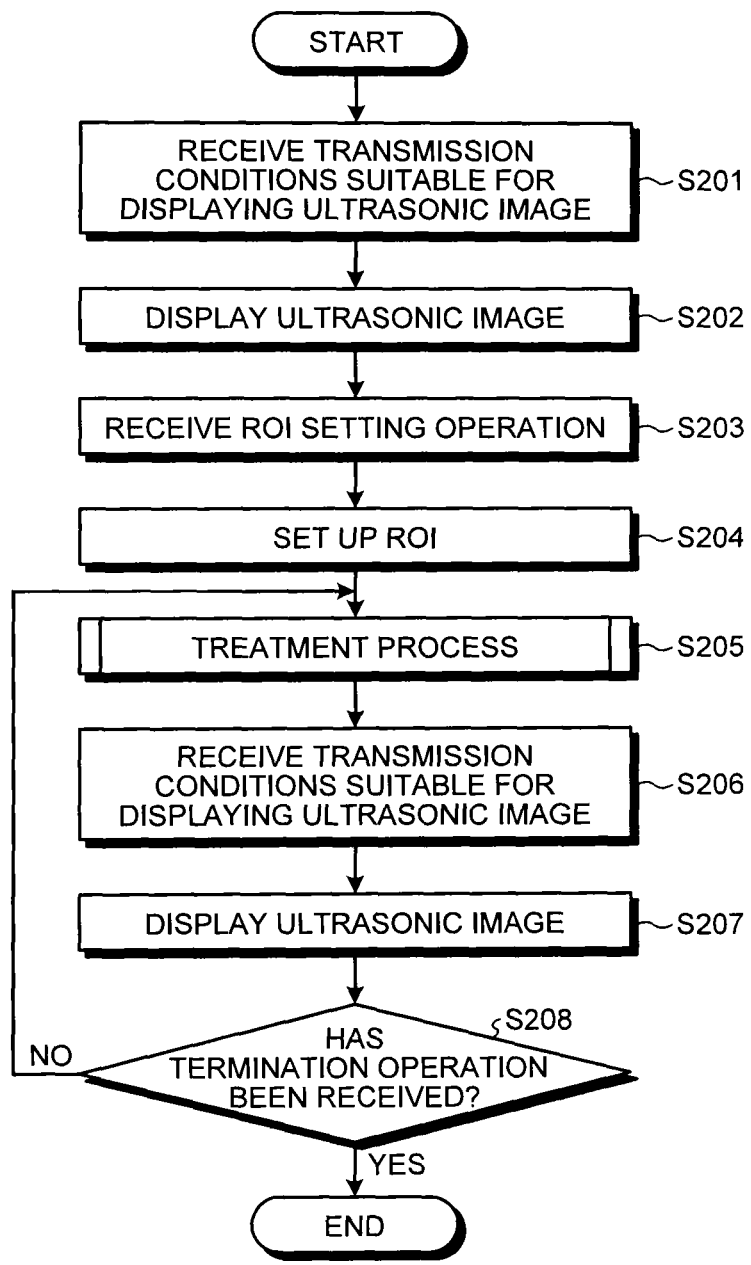
FIG. 7 is a flowchart of an example procedure of a process performed by the ultrasound apparatus according to the first embodiment.

Next, a usage example of the ultrasound apparatus 1 according to the first embodiment is explained with reference to FIG. 7. FIG. 7 is a flowchart of an example procedure of the process performed by the ultrasound apparatus 1 according to the first embodiment.

In the example of FIG. 7, first, when the operator operates the input device 20, the ultrasound apparatus 1 receives an ultrasonic transmission condition that is suitable for displaying an ultrasonic image (step S201). Then, the ultrasound apparatus 1 generates an ultrasonic image of the subject P, and displays the generated ultrasonic image onto the monitor 30 (step S202).

Thereafter, when the operator operates the input device 20, the ultrasound apparatus 1 receives a ROI setting request (step S203). Then, the ultrasound apparatus 1 sets a ROI up in accordance with the ROI setting request (step S204).

Next, the ultrasound apparatus 1 executes a treatment process (step S205). This treatment process is the one illustrated in FIG. 6. That is, the ultrasound apparatus 1 makes the operator set a transmission condition for each scanning line, and transmits an ultrasound wave to the subject P in accordance with the set-up transmission condition for each scanning line. For example, the ultrasound apparatus 1 transmits the ultrasound wave to the subject P in accordance with the ultrasonic transmission conditions illustrated in FIG. 3, and thereby conducts treatment onto the subject P.

Then, the ultrasound apparatus 1 receives an ultrasonic transmission condition suitable for displaying an ultrasonic image (step S206). For example, the ultrasound apparatus 1 receives ultrasonic transmission conditions illustrated in FIG. 4, transmits an ultrasound wave to the subject P in accordance with the transmission conditions, and thereby generates an ultrasonic image of the subject P. Then, the ultrasound apparatus 1 displays the generated ultrasonic image onto the monitor 30 (step S207). In this manner, the ultrasound apparatus 1 can display an ultrasonic image that clearly presents the blood flowing state of small blood vessels. In such a manner, the operator of the ultrasound apparatus 1 observes the ultrasonic image and thereby sees whether the medical substance is effectively administered to the subject P.

Then, the ultrasound apparatus 1 determines whether a termination operation is received (step S208). Here, when a termination operation is not yet received (no at step S208), the ultrasound apparatus 1 returns to step S205. On the other hand, when a termination operation is received (yes at step S208), the ultrasound apparatus 1 terminates the process.

As discussed above, according to the first embodiment, the ultrasound apparatus 1 includes the receiving unit 191 that receives an ultrasonic transmission condition for each scanning line and the probe controlling unit 192 that controls the ultrasound probe 10 in such a manner as to transmit an ultrasound wave in accordance with the transmission condition received by the receiving unit 191 for each scanning line, and therefore it can accelerate the permeation of genes and medicinal substances into a specific site by use of microbubbles.

For example, when a medicinal substance is contained in the microbubbles, the ultrasound apparatus 1 can accelerate the permeation of the medicinal substance into a specific treatment site. In addition, for example, the ultrasound apparatus 1 can accelerate the permeation of microbubbles into a site such as capillaries, and as a result, it can generate an ultrasonic image that clearly depicts the blood flowing state of small blood vessels. As discussed above, with the ultrasound apparatus 1 according to the first embodiment, the operator can set ultrasonic transmission conditions for individual scanning lines. Thus, ultrasonic transmission conditions can be flexibly set up in accordance with the shape of the treatment site or the like so as to be suitable for the treatment site. Furthermore, because the ultrasound apparatus 1 according to the first embodiment can set ultrasonic transmission conditions for individual scanning lines, an ultrasound wave of a high sound pressure can be applied, for example, to the treatment site only, while applying an ultrasound wave of a low sound pressure to a site other than the treatment site.

Figure 8:
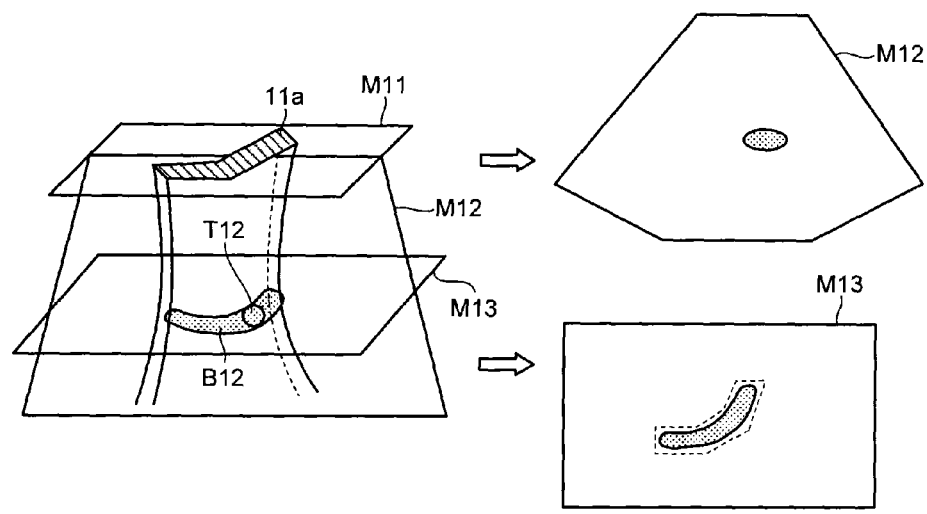
FIG. 8 is a diagram for explaining the process performed by the ultrasound apparatus when the ultrasound wave is three-dimensionally transmitted.

In the above, examples in which ultrasound waves are two-dimensionally transmitted by the ultrasound probe 10 have been explained, as illustrated in FIGS. 3 to 5. The ultrasound apparatus 1 according to the first embodiment, however, is also applicable to three-dimensional transmission of ultrasound waves by the ultrasound probe 10. This is now explained in detail with reference to FIG. 8. FIG. 8 is a diagram for explaining a process performed by the ultrasound apparatus 1 when ultrasound waves are three-dimensionally transmitted.

The ultrasound apparatus 1 explained below includes, as the ultrasound probe 10, for example, a mechanical scan probe that mechanically vibrates an ultrasound probe having multiple piezoelectric vibrators that are linearly arranged, an ultrasound probe having multiple piezoelectric vibrators that are arranged in a matrix form, or the like. The ultrasound apparatus 1 having such an ultrasound probe 10 generates a volume image that is a three-dimensional ultrasonic image in time series, and displays the generated volume image.

In the example of FIG. 8, the ultrasound probe 10 includes piezoelectric vibrators on a transmission surface M11 from which the ultrasound waves are emitted. In the example of FIG. 8, the ultrasound apparatus 1 causes the piezoelectric vibrators arranged in a two-dimensional region 11a among the piezoelectric vibrators of the ultrasound probe 10 to transmit an ultrasound wave in accordance with specific transmission conditions, and thereby accelerates the permeation of genes and medical substances into a blood vessel B12 that is three-dimensionally curved. A tomographic image of a surface M12 is presented in the upper right of FIG. 8, and a tomographic image of a surface M13 is presented in the lower right of FIG. 8.

Here, the ultrasound apparatus 1 can set transmission conditions for individual scanning lines of an ultrasound wave that is three-dimensionally transmitted by the ultrasound probe 10. Then, when an ultrasonic transmission conditions are set up for each scanning line, the ultrasound apparatus 1 controls the ultrasound probe 10 in such a manner as to transmit ultrasound waves in accordance with the transmission conditions for each scanning line. For example, regarding the blood vessel B12 of FIG. 8, the ultrasound apparatus 1 can apply ultrasound waves of different transmission conditions to a site T12 and to a site other than the site T12. In this manner, the ultrasound apparatus 1 can apply an ultrasound wave required for treatment or the like to a specific site only of a treatment target that spreads three-dimensionally in any shape.

Figure 9:
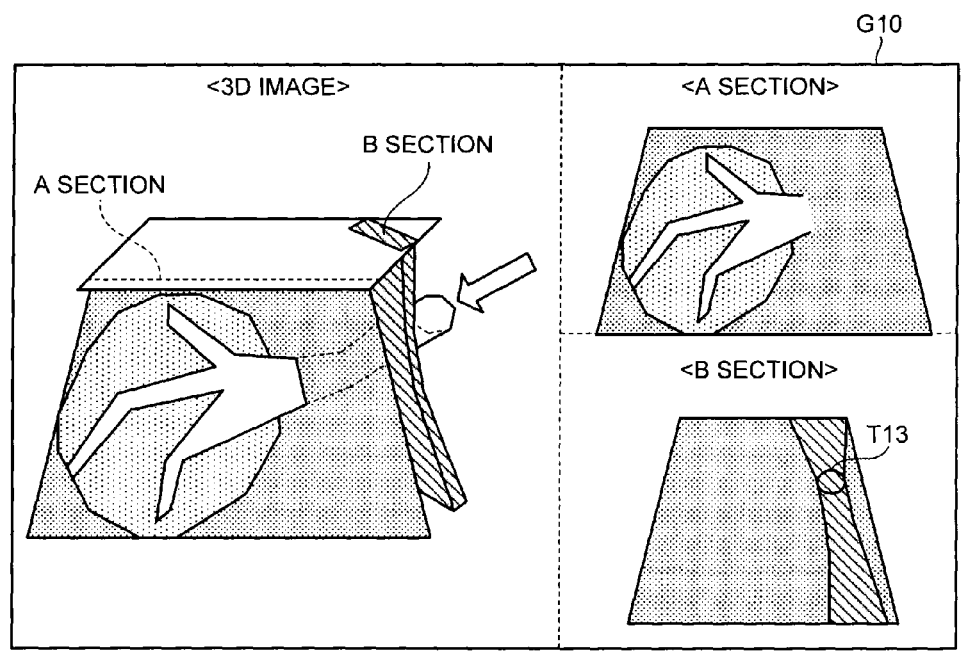
FIG. 9 is a diagram for showing an example screen on which a volume image and cross-sectional images are displayed in parallel.

Moreover, the controlling unit 190 of the ultrasound apparatus 1 according to the first embodiment may perform control so that a volume image and a tomographic image of the subject P are displayed on the same screen. This is explained in detail with reference to FIG. 9. FIG. 9 is a diagram for showing an example screen on which a volume image and tomographic images are displayed in parallel. On the screen G10 illustrated in FIG. 9, a volume image is displayed in an area with a header <Three-dimensional Image>, a tomographic image of the A section of the volume image is displayed in an area with a header <A Section>, and a tomographic image of the B section of the volume image is displayed in an area with a header <B Section>.

The ultrasound apparatus 1 makes the operator set the position of a section of the volume image, and displays a tomographic image of the set-up section position onto the screen G10. Then, with the screen G10 displayed, the ultrasound apparatus 1 receives transmission conditions of a three-dimensionally transmitted ultrasound wave for each scanning line from the operator. In the example of FIG. 9, the operator is to apply a treatment ultrasound wave to the site T13 that is displayed on the B-section tomographic image, for example. In this situation, because the controlling unit 190 performs control to display the screen G10, the operator can set the ultrasonic transmission conditions for each scanning line while checking the entire treatment site on the volume image and also checking the site to which the treatment ultrasound wave is applied on the tomographic image.

Second Embodiment

According to the first embodiment, an example in which ultrasonic transmission conditions can be set up for individual scanning lines has been explained. According to the second embodiment, an example in which the aperture or deflection or deflection of the ultrasound probe 10 can be set up is explained.

Figure 10:
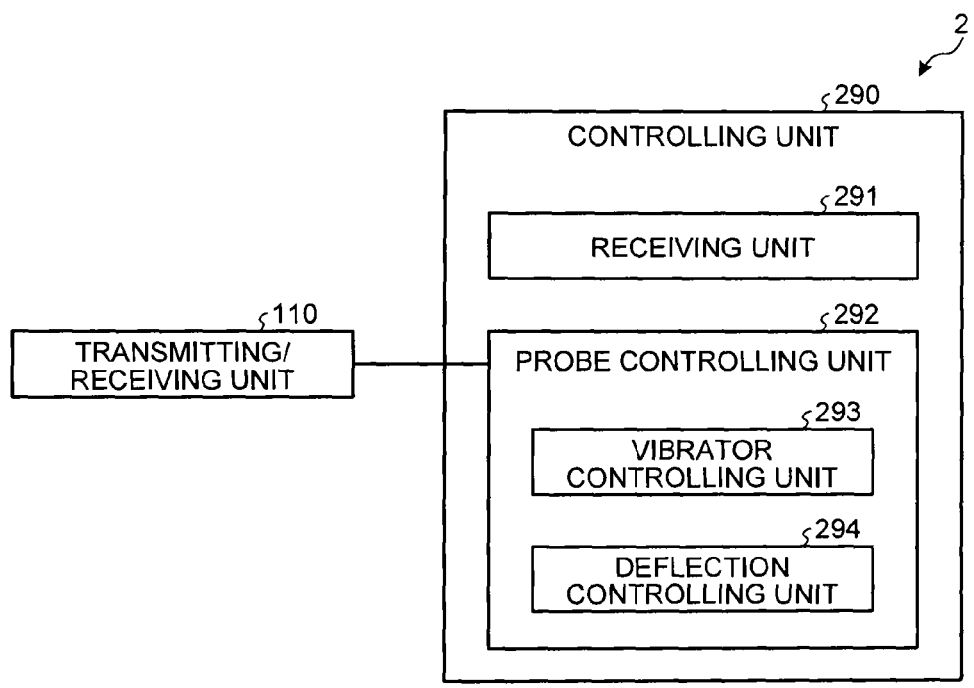
FIG. 10 is a block diagram for showing an example structure of the controlling unit according to the second embodiment.

First, a controlling unit 290 according to the second embodiment is explained with reference to FIG. 10. FIG. 10 is a block diagram for showing an example structure of the controlling unit 290 according to the second embodiment. The entire structure of an ultrasound apparatus 2 according to the second embodiment is the same as the example structure indicated in FIG. 1, and therefore the explanation is omitted here. The ultrasound probe 10 connected to the ultrasound apparatus 2 according to the second embodiment has multiple piezoelectric vibrators arranged in a matrix form, and transmits ultrasound waves into three-dimensional space.

As illustrated in FIG. 10, the controlling unit 290 includes a receiving unit 291 and a probe controlling unit 292. The receiving unit 291 receives, as ultrasonic transmission conditions, the setting of an aperture that determines a piezoelectric vibrator of the piezoelectric vibrators included in the ultrasound probe 10 that is to send an ultrasound wave, the setting of the deflection of the ultrasound wave transmitted from the ultrasound probe 10 to the subject P, and the setting of a ROI in the subject P.

For example, when the operator performs an operation of selecting an aperture of the ultrasound probe 10 by way of the input device 20, the receiving unit 291 receives the setting of the aperture from the input device 20. Furthermore, for example, when the operator performs an operation of setting the deflection of the ultrasound wave by way of the input device 20, the receiving unit 291 receives the setting of the deflection of the ultrasound wave from the input device 20. Moreover, for example, when the operator performs an operation of setting a ROI by way of the input device 20, the receiving unit 291 receives the setting of the ROI from the input device 20.

The probe controlling unit 292 includes a vibrator controlling unit 293 and a deflection controlling unit 294.

When the receiving unit 291 receives the setting of the aperture of the ultrasound probe 10, the vibrator controlling unit 293 controls the ultrasound probe 10 in such a manner as to transmit an ultrasound wave through the aperture specified by the setting.

When the receiving unit 291 receives the setting of the deflection of the ultrasound wave, the deflection controlling unit 294 controls the ultrasound probe 10 in such a manner as to transmit the ultrasound wave with the deflection specified by the setting.

An example of the process performed by the controlling unit 290 according to the second embodiment is explained with reference to FIG. 11. FIG. 11 is a diagram for explaining an example of the process performed by the controlling unit 290 according to the second embodiment. In the example of FIG. 11, it is assumed that the ultrasound probe 10 first applies an ultrasound wave to a treatment site T21 from a piezoelectric vibrator that is arranged in an aperture area 21a. Here, if there is a bone between the aperture area 21a and the treatment site T21, the ultrasound wave transmitted from the piezoelectric vibrator that is arranged in the aperture area 21a is almost totally reflected. For this reason, the ultrasound wave transmitted from the piezoelectric vibrator that is arranged in the aperture area 21a is barely applied to the treatment site T21. In the following description, the site of a bone or the like that obstructs the passage of the ultrasound wave may be referred to as an "obstruction site".

Here, the ultrasound apparatus 2 according to the second embodiment makes the operator set up an aperture of the ultrasound probe 10. For example, the operator performs an operation of changing the aperture of the ultrasound probe 10 from the aperture area 21a to an aperture area 21b. In such a situation, the vibrator controlling unit 293 of the probe controlling unit 292 controls the ultrasound probe 10 to transmit an ultrasound wave from a piezoelectric vibrator arranged in the aperture area 21b.

In addition, the ultrasound apparatus 2 according to the second embodiment makes the operator set the deflection of the ultrasound wave transmitted by the ultrasound probe 10. For example, when the ultrasound wave is being transmitted from the piezoelectric vibrator that is arranged in the aperture area 21b, the operator sets the deflection of the ultrasound wave to apply the ultrasound wave to the treatment site T21. In such a situation, the deflection controlling unit 294 of the probe controlling unit 292 controls the ultrasound probe 10 so that the scanning line L21 of the ultrasound wave is changed to the scanning line L22, as illustrated in the bottom of FIG. 11.

As discussed above, according to the second embodiment, the ultrasound apparatus 2 includes the receiving unit 291 that receives the setting of the aperture or deflection of the ultrasound probe or the setting of the ROI, the vibrator controlling unit 293 that controls the ultrasound probe 10 in such a manner as to transmit an ultrasound wave through the aperture received by the receiving unit 291, and the deflection controlling unit 294 that controls the ultrasound probe 10 in such a manner as to transmit the ultrasound wave with the deflection received by the receiving unit 291. Thus, even if there is an obstruction site between the ultrasonic transmission surface and the treatment site, the ultrasound waves can be applied to the treatment site.

Third Embodiment

According to the second embodiment, an example in which the operator sets the aperture or deflection of the ultrasound probe 10 has been explained. According to the third embodiment, an example in which the ultrasound apparatus determines whether there is an obstruction site and, if there is an obstruction site or the like, adjusts the aperture or deflection of an ultrasound wave is explained.

Figure 12:
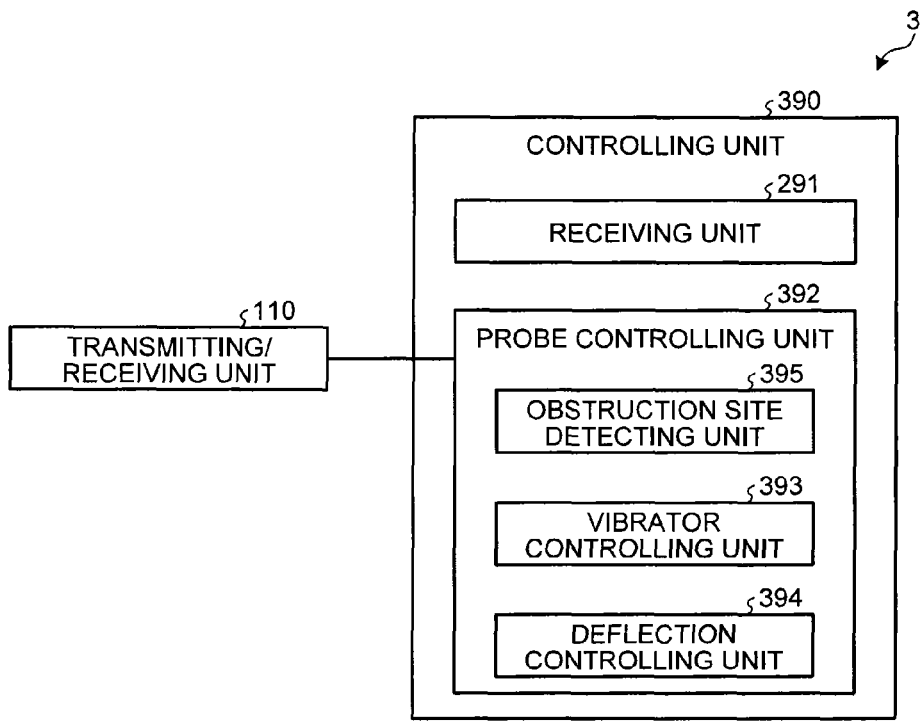
FIG. 12 is a block diagram for showing an example structure of the controlling unit according to the third embodiment.

First, a controlling unit 390 according to the third embodiment is explained with reference to FIG. 12. FIG. 12 is a block diagram for showing an example structure of the controlling unit 390 according to the third embodiment. The entire structure of an ultrasound apparatus 3 according to the third embodiment is the same as the example structure of FIG. 1, and thus the explanation is omitted here. In the following description, a component that has a function similar to that of a structural component that has been explained above is given the same reference numeral, and the detailed explanation is omitted.

As illustrated in FIG. 12, the controlling unit 390 includes the receiving unit 291 and a probe controlling unit 392. The probe controlling unit 392 controls the ultrasound probe 10 based on the settings prepared by the operator for the aperture of the ultrasound probe 10 and the ROI in such a manner as to transmit the ultrasound wave from the piezoelectric vibrator of the set-up aperture onto the ROI. This probe controlling unit 392 includes an obstruction site detecting unit 395, a vibrator controlling unit 393, and a deflection controlling unit 394.

The obstruction site detecting unit 395 determines whether there is an obstruction site between the transmission surface of the ultrasound probe 10 from which the ultrasound wave is transmitted and the ROI. For example, the obstruction site detecting unit 395 compares reception signals of the transmission OFF time and the transmission ON time and thereby detects a region that the ultrasound wave does not reach due to an obstacle such as a rib bone. The obstruction site detecting unit 395 may also compare the ultrasound wave transmitted by the ultrasound probe 10 and the received reflection wave signal to determine whether the ultrasound wave transmitted by the ultrasound probe 10 is almost totally reflected. Then, if the ultrasound wave is almost totally reflected, the obstruction site detecting unit 395 determines that there is an obstruction site between the transmission surface of the ultrasound probe 10 and the ROI.

Moreover, if there is an obstruction site between the transmission surface of the ultrasound probe 10 from which the ultrasound wave is transmitted and the ROI, the ultrasound wave is substantially totally reflected from the obstruction site, and therefore an image of the ROI does not appear in the ultrasonic image. Thus, the obstruction site detecting unit 395 may calculate, for example, the brightness of the ultrasonic image generated by the image generating unit 140, determine that an image of the ROI located in the depth direction from the obstruction site does not appear if the brightness of the ROI is lower than a predetermined threshold value, and detect the obstruction site.

The vibrator controlling unit 393 changes the aperture of the ultrasound probe 10 when the obstruction site detecting unit 395 detects an obstruction site. The vibrator controlling unit 393 may change piezoelectric vibrators for ultrasonic transmission at random, or change them in order in accordance with certain areas.

When the obstruction site detecting unit 395 detects an obstruction site, the deflection controlling unit 394 changes the deflection of the ultrasound wave in such a manner as to apply the ultrasound wave transmitted by the ultrasound probe 10 to the ROI. For example, in the example of FIG. 11, the vibrator controlling unit 393 changes the piezoelectric vibrators for ultrasonic transmission, from the piezoelectric vibrator arranged in the aperture area 21a to the piezoelectric vibrators arranged in the aperture area 21b. In such a situation, the deflection controlling unit 394 changes the deflection of the ultrasound wave so that the scanning line L21 of the ultrasound wave is changed to the scanning line L22.

The obstruction site detecting unit 395 performs the process of determining whether there is an obstruction site between the transmission surface of the ultrasound probe 10 and the ROI, after the vibrator controlling unit 393 and the deflection controlling unit 394 change the aperture and the deflection of the ultrasound probe 10. Then, when the obstruction site detecting unit 395 detects an obstruction site, the vibrator controlling unit 393 and the deflection controlling unit 394 changes the aperture and the deflection of the ultrasound probe 10 again. In other words, the obstruction site detecting unit 395, the vibrator controlling unit 393, and the deflection controlling unit 394 repeat the process until the ultrasound wave is applied to the ROI without being reflected from the obstruction site.

As described above, according to the third embodiment, the ultrasound apparatus 3 includes the obstruction site detecting unit 395 that determines whether there is an obstruction site between the ultrasonic transmission surface and the ROI, the vibrator controlling unit 393 that changes the aperture of the ultrasound probe 10 when the obstruction site detecting unit 395 detects an obstruction site, and the deflection controlling unit 394 that changes the deflection of the ultrasound wave when the obstruction site detecting unit 395 detects an obstruction site. Hence, even when there is an obstruction site between the ultrasonic transmission surface and the treatment site, ultrasound waves can be applied to the treatment site without requiring any operation from the operator.

According to the second and third embodiments, the ultrasound probe 10 having multiple piezoelectric vibrators arranged in a matrix has been dealt with as an example, but the ultrasound apparatuses 2 and 3 may be connected to a mechanical scan probe. In such a situation, the ultrasound apparatuses 2 and 3 may change the aperture of the mechanical scan probe.

In addition, according to the third embodiment, the obstruction site detecting unit 395, the vibrator controlling unit 393, and the deflection controlling unit 394 may repeat the above process to find a combination of the aperture and the deflection with which the passage can avoid an obstruction site. Then, if there is more than one combination of the aperture and the deflection for avoiding an obstruction site, the vibrator controlling unit 393 and the deflection controlling unit 394 may select a passage with the smallest deflection angle from among the multiple combinations, and change the aperture and the deflection of the ultrasound probe 10. In this manner, by selecting a passage with a small deflection angle, the vibrator controlling unit 393 and the deflection controlling unit 394 can improve the application efficiency with respect to the ROI and can also reduce artifacts. Moreover, when there is more than one combination of the aperture and the deflection for avoiding an obstruction site, the controlling unit 390 presents these combinations to the operator so that the operator can select which combination of the aperture and deflection to be adopted to transmit the ultrasound wave.

Fourth Embodiment

According to the first embodiment, an example in which the operator sets up ultrasonic transmission conditions has been discussed. According to the fourth embodiment, an example in which the ultrasound apparatus holds multiple patterns of ultrasonic transmission conditions so that the operator can select a transmission condition pattern therefrom is explained.

Figure 13:
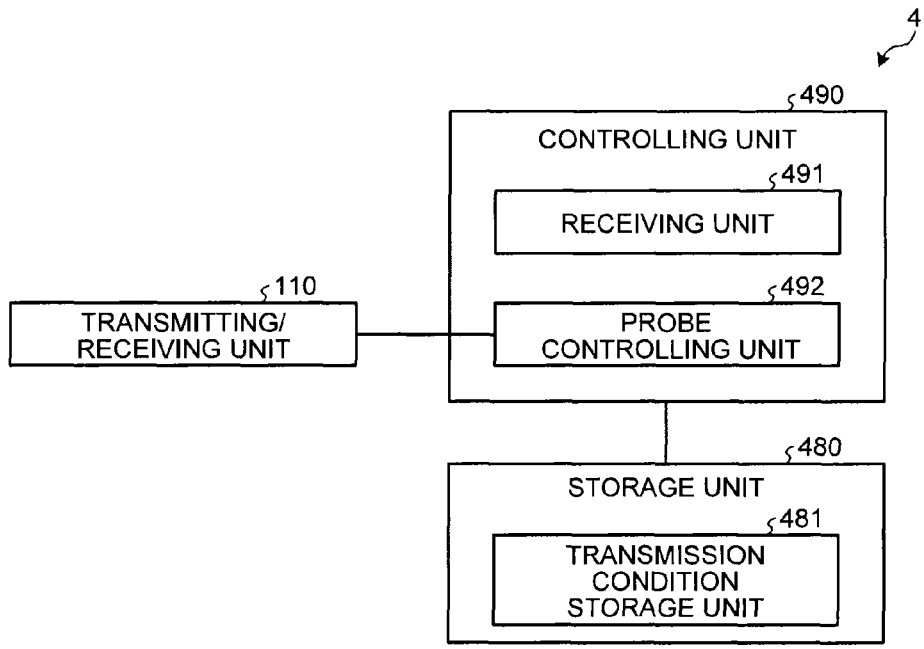
FIG. 13 is a block diagram for showing an example structure of a storage unit and the controlling unit according to the fourth embodiment.

First, a storage unit 480 and a controlling unit 490 according to the fourth embodiment are explained with reference to FIG. 13. FIG. 13 is a block diagram for showing an example structure of the storage unit 480 and the controlling unit 490 according to the fourth embodiment. The entire structure of an ultrasound apparatus 4 according to the fourth embodiment is the same as the example structure of FIG. 1, and thus the explanation is omitted here.

As illustrated in FIG. 13, the storage unit 480 includes a transmission condition storage unit 481. The transmission condition storage unit 481 stores therein multiple groups of transmission conditions for individual scanning lines included in a predetermined scanning area. An example of the transmission condition storage unit 481 is indicated in FIG. 14. As shown in FIG. 14, the transmission condition storage unit 481 stores therein ultrasonic transmission conditions for individual scanning lines in accordance with different patterns. Here, a pattern means a type of a group of transmission conditions for different scanning lines. Furthermore, a scanning line means a scanning line of an ultrasound wave transmitted by the ultrasound probe 10. In addition, a transmission condition indicates a condition for transmitting an ultrasound wave from the ultrasound probe 10. In the example of FIG. 14, the transmission condition storage unit 481 stores therein sound pressures, frequencies, and pulse repetition frequencies (PRFs) of ultrasound waves as transmission conditions.

The transmission condition storage unit 481 illustrated in FIG. 14 stores therein, as a pattern "PT11", a sound pressure "P10", a frequency "F5", and a PRF "RF10" for the ultrasound wave in scanning lines L11 to L15. The ultrasonic transmission conditions corresponding to the pattern "PT11" are the same as the ultrasonic transmission conditions of FIG. 3. In addition, the ultrasonic transmission conditions described as a pattern "PT12" are the same as the ultrasonic transmission conditions of FIG. 4. Moreover, the ultrasonic transmission conditions described as a pattern "PT13" are the same as the ultrasonic transmission conditions of FIG. 5.

To return to the explanation of FIG. 13, the controlling unit 490 includes a receiving unit 491 and a probe controlling unit 492. The receiving unit 491 receives a pattern selected from the patterns of transmission condition groups stored in the transmission condition storage unit 481. More specifically, when the operator conducts an operation of selecting transmission conditions, the controlling unit 490 displays the patterns and transmission conditions illustrated in FIG. 14 onto the monitor 30 so that the operator can select a pattern. Then, the receiving unit 491 receives the transmission condition pattern selected by the operator from the input device 20 or the like.

The receiving unit 491 may receive a transmission condition pattern and also receive the position of the ROI to place the scanning lines included in the selected transmission condition pattern. It is assumed, for example, that the operator selects the pattern PT11 in FIG. 14. In such a situation, the receiving unit 491 may receive a position in the ROI where to place the scanning lines L11 to L15 included in the pattern PT11. Here, the receiving unit 491 may receive the position in the ROI where to place some of the scanning lines L11 to L1. For example, the receiving unit 491 may receive the position of the scanning line L11 being on the left end of the ROI and the position of the scanning line L15 being on the right end of the ROI.

When the receiving unit 491 receives a pattern of the transmission condition groups, the probe controlling unit 492 controls the ultrasound probe 10, based on the transmission conditions corresponding to this pattern.

It is assumed, for example, that the operator selects a pattern PT12 of FIG. 14, and performs an operation of positioning the scanning line L11 on the right end of the ROI and the scanning line L15 on the left end of the ROI. In such a situation, the probe controlling unit 492 controls the ultrasound probe 10 in such a manner as to transmit an ultrasound wave of the sound pressure "P10", the frequency "F5", and the pulse repetition frequency "RF5" to the right end of the ROI, as illustrated in FIG. 4. In addition, the probe controlling unit 492 controls the ultrasound probe 10 in such a manner as to transmit an ultrasound wave of the sound pressure "P5" and the pulse repetition frequency "RF5" to the second one from the right end of the ROI and the rest. Here, the probe controlling unit 492 controls the ultrasound probe 10 so that the ultrasound wave transmitted to the left end of the ROI has the frequency of "F9" and that the frequency of the ultrasound wave increases linearly from the right end of the ROI to the left end of the ROI.

Next, the procedure of the process performed by the controlling unit 490 according to the fourth embodiment is explained, with reference to FIG. 15. FIG. 15 is a flowchart for showing an example of the procedure of the process performed by the controlling unit 490 according to the fourth embodiment.

As indicated in FIG. 15, the controlling unit 490 of the ultrasound apparatus 4 determines whether the operator performs an operation of selecting a transmission condition (step S301). Here, if the operator does not perform an operation of selecting a transmission condition (no at step S301), the controlling unit 490 goes into standby mode.

On the other hand, when the operator performs an operation of selecting a transmission condition (yes at step S301), the controlling unit 490 controls and displays the patterns and the transmission conditions stored in the transmission condition storage unit 481 onto the monitor 30 (step S302). In this manner, the controlling unit 490 makes the operator select a transmission condition pattern.

Then, the receiving unit 491 of the controlling unit 490 determines whether a pattern selected by the operator is received (step S303). Here, if no transmission condition pattern is received (no at step S303), the receiving unit 491 goes into standby mode.

On the other hand, when the receiving unit 491 receives an operation of selecting a transmission condition pattern (yes at step S303), the probe controlling unit 492 controls the ultrasound probe 10, based on the selected transmission condition pattern (step S304).

As described above, according to the fourth embodiment, the ultrasound apparatus 4 includes the transmission condition storage unit 481 that stores therein multiple patterns of transmission condition groups for different scanning lines, and the probe controlling unit 492 that controls the ultrasound probe 10, based on transmission condition groups for different scanning lines that correspond to the pattern selected by the operator. Thus, without requiring the setting up of transmission conditions for different scanning lines by the operator, an ultrasound wave can be transmitted for each scanning line in accordance with specific transmission conditions.

For example, if the transmission conditions indicated in FIGS. 3 to 5 are stored as patterns, as in the transmission condition storage unit 481 illustrated in FIG. 14, the operator can select one of the transmission condition patterns corresponding to FIGS. 3 to 5. In this manner, the ultrasound apparatus 4 can transmit an ultrasound wave in accordance with the transmission conditions of FIGS. 3 to 5 only by making the operator select a transmission condition pattern, and thus can accelerate the permeation of genes or medicinal substances into a specific site.

Fifth Embodiment

According to the fourth embodiment, an example in which the operator selects an ultrasonic transmission condition pattern has been explained. According to the fifth embodiment, an example in which the operator selects a transmission condition pattern and also sets up ultrasonic transmission conditions for some of the scanning lines is explained.

First, a storage unit 580 and a controlling unit 590 according to the fifth embodiment are explained, with reference to FIG. 16. FIG. 16 is a block diagram for explaining an example structure of the storage unit 580 and the controlling unit 590 according to the fifth embodiment. The entire structure of an ultrasound apparatus 5 according to the fifth embodiment is the same as the example structure of FIG. 1, and therefore the explanation is omitted here.

As illustrated in FIG. 16, the storage unit 580 includes a decision condition storage unit 581. When transmission conditions are determined for part of the scanning lines included in a specific scanning area, the decision condition storage unit 581 stores therein determination conditions for determining transmission conditions for scanning lines other than the part of the scanning lines.

In FIG. 17, an example of the decision condition storage unit 581 is illustrated. As illustrated in FIG. 17, the decision condition storage unit 581 stores therein determination conditions for different scanning lines in accordance with patterns. Here, items such as "arbitrary", "others", "right end", and "light end" are stored as the scanning lines in the decision condition storage unit 581. The "arbitrary" stored as a scanning line indicates any arbitrary scanning line transmitted to the ROI, while the "other" indicates any scanning line other than the scanning lines stored for the same pattern. The "right end" indicates any scanning line that is transmitted to the right end of the ROI, while the "light end" indicates any scanning line that is transmitted to the left end of the ROI.

With the pattern "PT21" in the decision condition storage unit 581 of FIG. 17, the operator sets the sound pressure, the frequency, and the pulse repetition frequency, and the set-up sound pressure, frequency, and pulse repetition frequency are adopted as the transmission conditions for an ultrasound wave that is to be transmitted to the ROI. In other words, in the pattern "PT21", all the sound pressures, frequencies, and pulse repetition frequencies of the ultrasound waves that are to be transmitted to the ROI have the same values for different scanning lines, and the operator is to set up the sound pressure, the frequency, and the pulse repetition frequency.

In addition, a pattern "PT22" in the decision condition storage unit 581 of FIG. 17 indicates that the sound pressures of the scanning lines at the right end and left end of the ROI are set up by the operator while the sound pressure of any scanning lines other than the right end and left end of the ROI is determined as "P5". Furthermore, the pattern "PT22" indicates that the frequencies of the scanning lines at the right end and left end of the ROI are set up by the operator and that the frequencies exhibit a linear relationship from the right end of the ROI to the left end of the ROI. In addition, the pattern "PT22" indicates that the pulse repetition frequency of the scanning line at the right end of the ROI is set up by the operator, and that the set-up pulse repetition frequency is adopted as the pulse repetition frequency for all the other scanning lines in the ROI.

To return to the explanation of FIG. 16, the controlling unit 590 includes a receiving unit 591 and a probe controlling unit 592. The receiving unit 591 receives an operation of selecting a pattern stored in the decision condition storage unit 581 and also receives an operation of setting a specific transmission condition. A "specific transmission condition" corresponds to any of the items in which "user setting" is entered as a determination condition in the decision condition storage unit 581 illustrated in FIG. 17.

More specifically, when the operator performs an operation of selecting transmission conditions, the controlling unit 590 makes the operator select a pattern by displaying the patterns and transmission conditions as shown in FIG. 17, and also makes the operator set up certain transmission conditions. Then, the receiving unit 591 receives the transmission condition pattern selected by the operator and the transmission conditions set up by the operator.

For example, the operator may select the pattern PT21 in the decision condition storage unit 581 of FIG. 17. In such a situation, the receiving unit 591 receives the pattern PT21 that has been selected, and also receives the sound pressure, frequency, and pulse repetition frequency that have been set up by the operator. Further, the operator may select the pattern PT22 in the decision condition storage unit 581 of FIG. 17. In such a situation, the receiving unit 591 receives the pattern PT22 that has been selected, and also receives the sound pressure, frequency, and pulse repetition frequency of the scanning line at the right end of the ROI and the sound pressure and frequency of the scanning line at the left end of the ROI.

When the receiving unit 591 receives a transmission condition pattern and specific transmission conditions, the probe controlling unit 592 determines the transmission conditions of the ultrasound wave that is to be transmitted to the ROI, and controls the ultrasound probe 10 in accordance with the determined transmission conditions.

For example, it is assumed that the receiving unit 591 receives the pattern PT21 of FIG. 17, and also receives the sound pressure "P10", the frequency "F10", and the pulse repetition frequency "RF10". In such a situation, the probe controlling unit 592 determines the sound pressure of the ultrasonic wave in all the scanning lines that are to be sent to the ROI as "P10", the frequency as "F10", and the pulse repetition frequency as "RF10", and controls the ultrasound probe 10 in such a manner as to transmit the ultrasound wave in accordance with these transmission conditions. In other words, the probe controlling unit 592 controls the ultrasound probe 10 to transmit the ultrasound wave in accordance with the transmission conditions of FIG. 3.

Furthermore, the receiving unit 591 receives the operation of selecting the pattern PT22 of FIG. 17, and also receives the operation of setting the sound pressure to "P10", the frequency to "F5", and the pulse repetition frequency to "RF10" for the scanning line of the "right end", and the sound pressure to "P5" and the frequency to "F9" for the scanning line of the "left end". In such a situation, the probe controlling unit 592 controls the ultrasound probe 10 to transmit the ultrasound wave in accordance with the transmission conditions of FIG. 4.

Next, the procedure of the process performed by the controlling unit 590 according to the fifth embodiment is explained with reference to FIG. 18. FIG. 18 is a flowchart for showing an example of the procedure of the process performed by the controlling unit 590 according to the fifth embodiment.

As indicated in FIG. 18, the controlling unit 590 of the ultrasound apparatus 5 determines whether the operator performs the operation of selecting the transmission conditions (step S401). Here, if the operator does not perform the operation of selecting the transmission conditions (no at step S401), the controlling unit 590 goes into standby mode.

On the other hand, if the operator performs the operation of selecting the transmission conditions (yes at step S401), the controlling unit 590 controls and displays transmission condition groups for each pattern stored in the decision condition storage unit 581, onto the monitor 30 (step S402). In this manner, the controlling unit 590 makes the operator select a transmission condition pattern and also set up certain transmission conditions.

Then, the receiving unit 591 of the controlling unit 590 determines whether the operation of selecting a transmission condition pattern and the operation of setting certain transmission conditions are received (step S403). Here, if the operation of selecting a transmission condition pattern or the like is not received (no at step S403), the receiving unit 591 goes into standby mode.

On the other hand, when the receiving unit 591 receives the operation of selecting a transmission condition pattern and the operation of setting certain transmission conditions (yes at step S403), the probe controlling unit 592 determines the transmission conditions of an ultrasound wave that is to be transmitted to the ROI, based on the transmission conditions set up by the operator and various kinds of information stored in the decision condition storage unit 581 (step S404). Then, the probe controlling unit 592 controls the ultrasound probe 10, based on the determined transmission conditions (step S405).

As described above, the ultrasound apparatus 5 according to the fifth embodiment includes the decision condition storage unit 581 that stores therein determination conditions for determining, based on the transmission conditions for some of scanning lines, transmission conditions for the other scanning lines, and the probe controlling unit 592 that determines transmission conditions based on the pattern selected by the operator and the transmission conditions of some of the scanning lines set up by the operator and controls the ultrasound probe 10 based on the determined transmission conditions. Hence, with simple setting up of transmission conditions by the operator, an ultrasound wave can be transmitted in accordance with specific transmission conditions for individual scanning lines.

The ultrasound apparatus according to the first to fifth embodiments may detect the movement of living tissue in a region of interest and transmit an ultrasound wave to follow the movement of the living tissue. More specifically, the ultrasound apparatus calculates a motion vector by use of multiple ultrasonic images of different time phases generated by the image generating unit 140, and thereby detects the movement of the living tissue based on the calculated motion vector. Then, the ultrasound apparatus changes the transmission conditions of the ultrasound waves transmitted to the region of interest in such a manner as to follow the movement of the living tissue. For example, in the example of FIG. 4, when detecting the movement of the treatment site T11 to the left by "α", the ultrasound apparatus may shift ultrasonic transmission conditions for the scanning lines L11 to L15 to the left by "α". For example, the sound pressure of the ultrasound wave in the scanning line L12 may be determined as "P10", and the frequency may be determined as "F5". In this manner, the ultrasound apparatus can apply the ultrasound wave to the site that the operator desires, in accordance with the transmission conditions set by the operator, even when the treatment site T11 moves in accordance with the movement of the body.

Moreover, the ultrasound apparatus according to the first to fifth embodiments may estimate, before transmission of the ultrasound wave in accordance with the transmission conditions set by the operator, the distribution of the ultrasound wave that is to be transmitted to the ROI in accordance with these transmission conditions. Then, the ultrasound apparatus may place the estimated distribution of the ultrasound wave onto the ultrasonic images generated by the image generating unit 140 and control and display it onto the monitor 30. For example, the ultrasound apparatus may control and display an ultrasonic image in which the ultrasound wave is expressed by arrows onto the monitor 30, as shown in the upper half of FIG. 5. Furthermore, for example, the ultrasound apparatus may control and display an ultrasonic image in which the distribution of the ultrasound wave is depicted onto the monitor 30, as shown in FIG. 11. In addition, the ultrasound apparatus according to the first to the fifth embodiments may control and display ultrasonic transmission conditions for individual scanning lines onto the monitor 30.

Moreover, in the examples according to the first to fifth embodiments, microbubbles containing a medicinal substance have been explained, but genes may be contained in the microbubbles. In other words, the ultrasound apparatus according to the first to fifth embodiments can accelerate the permeation of medicinal substances and genes into cells. Examples of substances contained in the microbubbles include genes, protein substances, substances in the body, medicinal substances, and nano-droplets.

Furthermore, the receiving unit and the probe controlling unit that are included in the controlling unit indicated in FIGS. 2, 10, 12, 13, and 16 may be realized by hardware such as an integrated circuit, or by a software program that is formed into modularized software.

According to at least one of the above embodiments, by incorporating a receiving unit that receives ultrasonic transmission conditions for individual scanning lines and a probe controlling unit that controls the ultrasound probe in such a manner as to transmit an ultrasound wave in accordance with the transmission conditions for the scanning lines, the permeation of genes and medical substances into a specific site can be accelerated by use of microbubbles.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound apparatus, comprising:
an ultrasound probe including vibrators configured to transmit and receive an ultrasound wave;
processing circuitry configured to:
receive settings in relation to an aperture of the ultrasound probe and a region of interest in a body of a subject to whom microbubbles are injected; and
control the ultrasound probe based on the settings received to transmit the ultrasound wave from a vibrator arranged in the aperture to the region of interest;
wherein
the processing circuitry controls the ultrasound wave transmitted by the ultrasound probe for each scanning line such that a frequency of the ultrasound wave gradually increases along a downstream direction of a bloodstream flow in the region of interest,
wherein the processing circuitry is further configured to control the ultrasound wave transmitted by the ultrasound probe for each scanning line such that a sound pressure of the ultrasound wave being transmitted to a site located upstream of bloodstream of a predetermined site is higher than a sound pressure of an ultrasound wave adopted for generating an ultrasound image, and a sound pressure of the ultrasound wave being transmitted to the predetermined site is the sound pressure of the ultrasound wave adopted for generating an ultrasound image.

2. The ultrasound apparatus according to claim 1, the processing circuitry further configured to:
determine whether there is an obstruction site that obstructs passage of the ultrasound wave between a transmission surface of the ultrasound probe through which the ultrasound wave is transmitted and the region of interest, and
detect the obstruction site, and change the aperture of the ultrasound probe or deflection of the ultrasound waves transmitted by the ultrasound probe such that the region of interest is irradiated with the ultrasound wave.

3. The ultrasound apparatus according to claim 1, wherein the processing circuitry is further configured to:
receive settings in relation to deflection of the ultrasound probe; and
change the deflection of the ultrasound probe based on the settings received to transmit the ultrasound wave to the region of interest.

4. The ultrasound apparatus according to claim 1, wherein the processing circuitry is further configured to:
generate a three-dimensional ultrasonic image of the subject by use of a reflection wave signal of the ultrasound wave transmitted by the ultrasound probe to the subject; and
control display of the three-dimensional ultrasonic image and one or more tomographic image of the three-dimensional ultrasonic image at a time.

5. The ultrasound apparatus according to claim 1, wherein the processing circuitry is further configured to:
generate an ultrasonic image of the subject by use of a reflection wave signal of the ultrasound wave transmitted by the ultrasound probe to the subject,
detect movement of the region of interest of the subject by use of a plurality of ultrasonic images generated, and control the ultrasound probe to follow the movement of the region of interest.

6. The ultrasound apparatus according to claim 1, wherein the processing circuitry is further configured to:
generate an ultrasonic image of the subject by use of a reflection wave signal of the ultrasound wave transmitted by the ultrasound probe to the subject;
control display of the ultrasonic image; and
receive settings in relation to a transmission condition of the ultrasound wave for each scanning line of the ultrasound wave transmitted by the ultrasound probe; and
when the processing circuitry receives the settings in relation to the transmission condition for each scanning line, the processing circuitry is further configured to estimate distribution of the ultrasound wave transmitted to the subject in accordance with the transmission condition for each scanning line, and display the estimated distribution of the ultrasound wave that is laid over the ultrasonic image.

7. The ultrasound apparatus according to claim 1, further comprising:
transmission condition storage circuitry configured to store therein a plurality of types of transmission condition groups for different scanning lines included in a predetermined scanning area,
wherein the processing circuitry receives a type that is selected from the types of the transmission condition groups stored in the transmission condition storage circuitry; and
controls the ultrasound probe in accordance with a transmission condition group corresponding to the type received.

8. The ultrasound apparatus according to claim 1, further comprising:
decision condition storage circuitry configured to, when a transmission condition is determined for part of scanning lines included a predetermined scanning area, store therein a determination condition for determining a transmission condition for scanning lines other than the part of the scanning lines,
wherein the processing circuitry receives settings in relation to the transmission condition for the part of the scanning lines and
the processing circuitry determines the transmission condition for the other scanning lines by use of the transmission condition for the part of the scanning lines and the determination condition stored in the decision condition storage circuitry, and controls the ultrasound probe based on the transmission condition that is determined for the other scanning lines and the transmission condition for the part of the scanning lines.

9. The ultrasound apparatus according to claim 1, wherein the processing circuitry is further configured to control the ultrasound wave transmitted by the ultrasound probe for each scanning line such that a pulse repetition of the ultrasound wave is higher than a pulse repetition frequency of an ultrasound wave adopted for generating an ultrasonic image.

10. The ultrasound apparatus according to claim 1, wherein
the processing circuitry is further configured to control the ultrasound wave transmitted by the ultrasound probe for each scanning line such that a pulse repetition frequency of the ultrasound wave is a pulse repetition frequency of an ultrasound wave adopted for generating an ultrasonic image.

11. The ultrasound apparatus according to claim 1, wherein
in the ultrasound probe the vibrators are two-dimensionally arranged.

12. An ultrasound apparatus controlling method executed by a computer, comprising:
receiving settings, by a processing circuitry, in relation to an aperture of an ultrasound probe having vibrators to transmit and receive an ultrasound wave and a region of interest in a body of a subject into whom microbubbles are injected;
controlling the ultrasound probe based on the settings to transmit the ultrasound wave from a vibrator arranged in the aperture to the region of interest;
controlling the ultrasound wave transmitted by the ultrasound probe for each scanning line such that a frequency of the ultrasound wave gradually increases along a downstream direction of a bloodstream flow in the region of interest; and
controlling, by the processing circuitry, the ultrasound wave transmitted by the ultrasound probe for each scanning line such that a sound pressure of the ultrasound wave being transmitted to a site located upstream of bloodstream of a predetermined site is higher than a sound pressure of an ultrasound wave adopted for generating an ultrasound image, and a sound pressure of the ultrasound wave being transmitted to the predetermined site is the sound pressure of the ultrasound wave adopted for generating an ultrasound image.

13. An ultrasound apparatus, comprising:
an ultrasound probe including vibrators configured to transmit and receive an ultrasound wave;
processing circuitry configured to:
receive settings in relation to an aperture of the ultrasound probe and a region of interest in a body of a subject to whom microbubbles are injected; and
control the ultrasound probe based on the settings received to transmit the ultrasound wave from a vibrator arranged in the aperture to the region of interest;
wherein the processing circuitry controls the ultrasound wave transmitted by the ultrasound probe for each scanning line such that a frequency of the ultrasound wave gradually increases along a downstream direction of a bloodstream flow in the region of interest,
wherein the processing circuitry is further configured to control the ultrasound wave transmitted by the ultrasound probe for each scanning line such that a pulse repetition frequency of the ultrasound wave is higher than a pulse repetition frequency of a ultrasound wave adopted for generating an ultrasonic image.

* * * * *